(12) United States Patent
Nakamura et al.

(10) Patent No.: US 11,999,804 B2
(45) Date of Patent: Jun. 4, 2024

(54) TREATMENT AGENT FOR LYSOSOMAL STORAGE DISEASE

(71) Applicants: FUJIFILM Corporation, Tokyo (JP); KYOTO PREFECTURAL PUBLIC UNIVERSITY CORPORATION, Kyoto (JP)

(72) Inventors: Kentaro Nakamura, Ashigarakami-gun (JP); Tsukasa Kitahashi, Ashigarakami-gun (JP); Rie Hando, Ashigarakami-gun (JP); Satoshi Gojo, Kyoto (JP); Daisuke Kami, Kyoto (JP)

(73) Assignees: FUJIFILM Corporation, Tokyo (JP); KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 0 days.

(21) Appl. No.: 16/729,017

(22) Filed: Dec. 27, 2019

(65) Prior Publication Data
US 2020/0199178 A1    Jun. 25, 2020

Related U.S. Application Data

(63) Continuation of application No. PCT/JP2018/024879, filed on Jun. 29, 2018.

(30) Foreign Application Priority Data

Jun. 30, 2017  (JP) ................. 2017-128893

(51) Int. Cl.
| | |
|---|---|
| C07K 7/06 | (2006.01) |
| A61K 9/16 | (2006.01) |
| A61K 35/28 | (2015.01) |
| A61K 35/33 | (2015.01) |
| A61K 38/00 | (2006.01) |
| A61P 43/00 | (2006.01) |
| C12N 5/00 | (2006.01) |

(52) U.S. Cl.
CPC ............... *C07K 7/06* (2013.01); *A61K 35/28* (2013.01); *A61K 35/33* (2013.01); *A61P 43/00* (2018.01); *C12N 5/0068* (2013.01); *A61K 9/16* (2013.01); *A61K 38/00* (2013.01); *C12N 2533/40* (2013.01)

(58) Field of Classification Search
None
See application file for complete search history.

(56) References Cited

U.S. PATENT DOCUMENTS

| | | | |
|---|---|---|---|
| 7,927,587 B2 | 4/2011 | Blazer et al. | |
| 2006/0188975 A1 | 8/2006 | Ramaswami | |
| 2010/0179130 A1 | 7/2010 | Schneider et al. | |
| 2011/0027237 A1 | 2/2011 | Vanguri et al. | |
| 2012/0329157 A1 * | 12/2012 | Nakamura | A61L 27/222 435/397 |
| 2013/0071441 A1 | 3/2013 | Iwazawa et al. | |
| 2014/0212393 A1 | 7/2014 | Blazar et al. | |
| 2017/0095595 A1 | 4/2017 | Nakamura | |
| 2017/0100519 A1 | 4/2017 | Iwazawa et al. | |
| 2017/0203005 A1 | 7/2017 | Iwazawa et al. | |

FOREIGN PATENT DOCUMENTS

| | | | |
|---|---|---|---|
| CN | 101808635 A | | 8/2010 |
| CN | 102858381 A | | 1/2013 |
| EP | 2543397 A1 | | 9/2013 |
| JP | 2007-513188 A | | 5/2007 |
| JP | 2007-514403 A | | 6/2007 |
| JP | 4313381 B2 | | 5/2009 |
| JP | 2014-12114 A | | 1/2014 |
| JP | 2015-134193 A | | 7/2015 |
| JP | 2015134193 | * | 7/2015 |
| WO | WO 98/11206 A2 | | 3/1998 |
| WO | WO 2011/108517 A1 | | 9/2011 |
| WO | WO 2014/125277 A1 | | 8/2014 |
| WO | WO 2015/194494 A1 | | 12/2015 |
| WO | WO 2016/052504 A1 | | 4/2016 |

OTHER PUBLICATIONS

Nagueh (Circulation. Sep. 23, 2014;130(13): 1081-90) (Year: 2014).*
Campbell et al. (Molecular Therapy vol. 5, No. 5, May 2002) (Year: 2002).*
Ohshima et al. (Proc Natl Acad Sci U S A. May 25, 1999;96(11):6423-7) (Year: 1999).*
Yokoi et al. (J Gene Med 2011; 13: 262-268) (Year: 2011).*
Nitkin et al. (Stem Cells Translational Medicine, 2017;6:539-565) (Year: 2017).*
Peters et al. (Biores Open Access. Jan. 1, 2015;4(1):75-88) (Year: 2015).*
Xia et al. (Plos One 8(10): e77493) (Year: 2013).*
Mayo Clinic (downloaded on Apr. 29, 2023 from URL:<https://www.mayoclinic.org/diseases-conditions/niemann-pick/diagnosis-treatment/drc-20355890>) (Year: 2023).*
Demczko (downloaded on Apr. 29, 2023 from URL: <https://www.merckmanuals.com/home/children-s-health-issues/hereditary-metabolic-disorders/tay-sachs-disease-and-sandhoff-disease>) (Year: 2023).*
Author Unknown, "CultiShper: Macroporous Gelatin Microcarriers", Percell Biolytica AB, XP055699770, URL: http://www.percell.se/inst_g.pdf, Jan. 1, 2020, 2 pages.
Extended European Search Report, dated Jun. 9, 2020, for corresponding European Application No. 18824444.6.

(Continued)

*Primary Examiner* — Sergio Coffa
(74) *Attorney, Agent, or Firm* — Birch, Stewart, Kolasch & Birch, LLP

(57) ABSTRACT

An object of the present invention is to provide an excellent treatment agent for a lysosomal storage disease. According to the present invention, there is provided a treatment agent for a lysosomal storage disease including a cell structure which includes a plurality of biocompatible polymer blocks and a plurality of cells of at least one type and in which at least one of the polymer blocks is disposed in gaps between the plurality of cells.

19 Claims, 15 Drawing Sheets

Specification includes a Sequence Listing.

(56) References Cited

OTHER PUBLICATIONS

International Preliminary Report on Patentability and English translation of the Written Opinion of the International Searching Authority (Forms PCT/IB/326, PCT/IB/373, and PCT/ISA/237) for International Application No. PCT/JP2018/024879, dated Jan. 9, 2020.
International Search Report (Form PCT/ISA/210) for International Application No. PCT/JP2018/024879, dated Aug. 7, 2018, with English translation.
Müüller et al., "In vitro analysis of multipotent mesenchymal stromal cells as potential cellular therapeutics in neurometabolic diseases in pediatric patients", Experimental Hematology, vol. 34, No. 10, 2006, pp. 1413-1419.
Ohashi, "Overcome the problem of therapies for lysosomal disease toward the development of cell and gene therapy", Jpn. J. Obstet. Gynecol. Neonatal. Hematol., vol. 22, No. 2, 2013, pp. 55-62, with English abstract.
Siddiqi et al., "Stem Cell Therapy for the Central Nervous System in Lysosomal Storage Diseases", Human Gene therapy, vol. 27, No. 10, 2016, pp. 749-757.
Japanese Office Action for Japanese Application No. 2019-527069, dated Jan. 26, 2021, with English translation.
Chinese Office Action and Search Report for corresponding Chinese Application No. 201880044009.9, dated Jul. 26, 2021, with English translation of the Office Action.
Chinese Office Action and Search Report for corresponding Chinese Application No. 201880044009.9, dated Feb. 18, 2022, with an English translation.
European Communication pursuant to Article 94(3) EPC for corresponding European Application No. 18824444.6, dated Feb. 14, 2022.
Taiwanese Office Action and Search Report for corresponding Taiwanese Application No. 107122617, dated May 12, 2022, with English translation.
Chinese Office Action for corresponding Chinese Application No. 201880044009.9, dated Sep. 13, 2022, with English translation.

* cited by examiner

FIG. 1
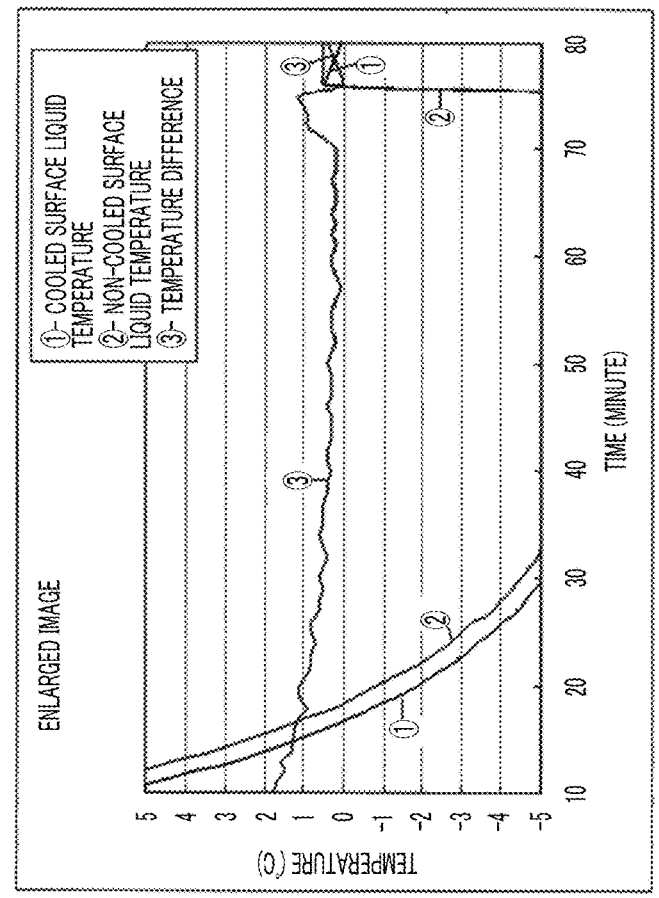
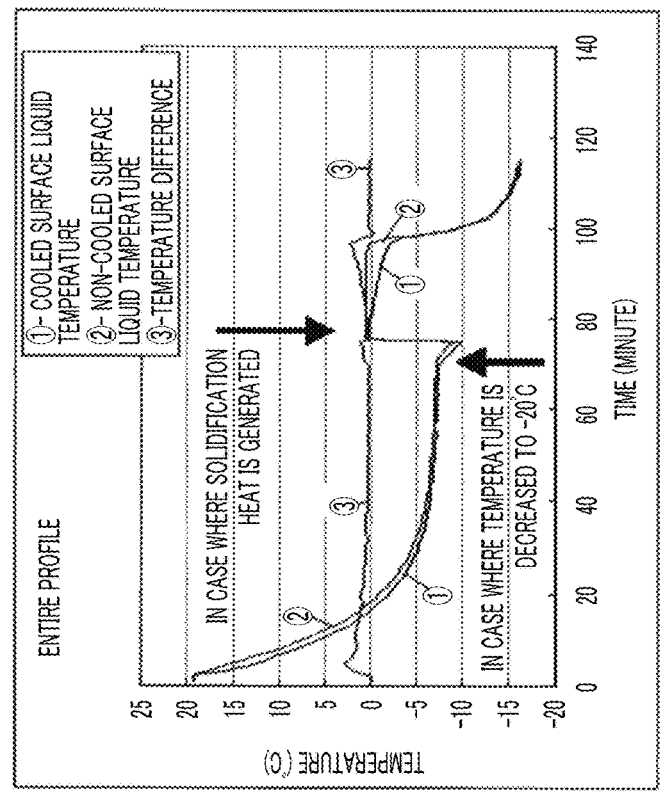

FIG. 2
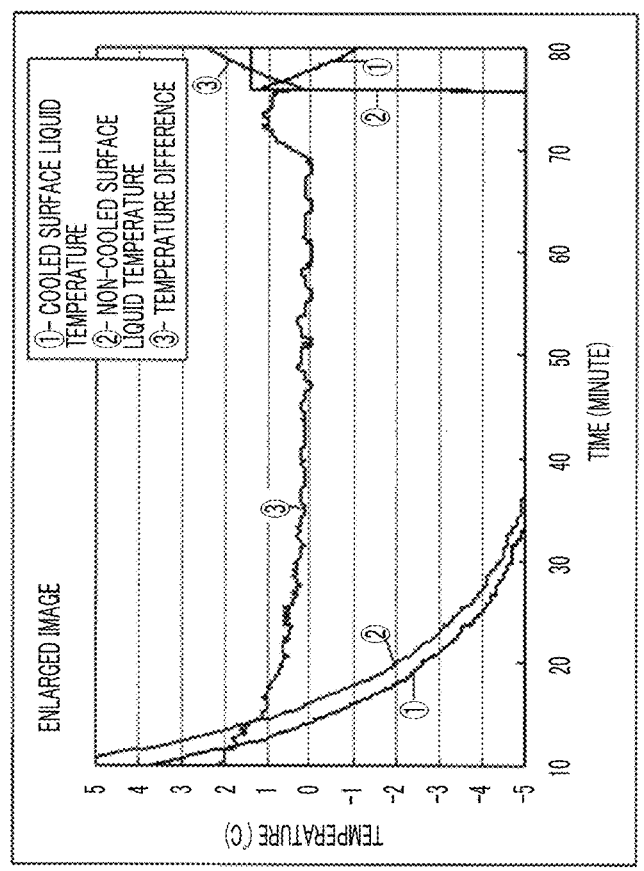
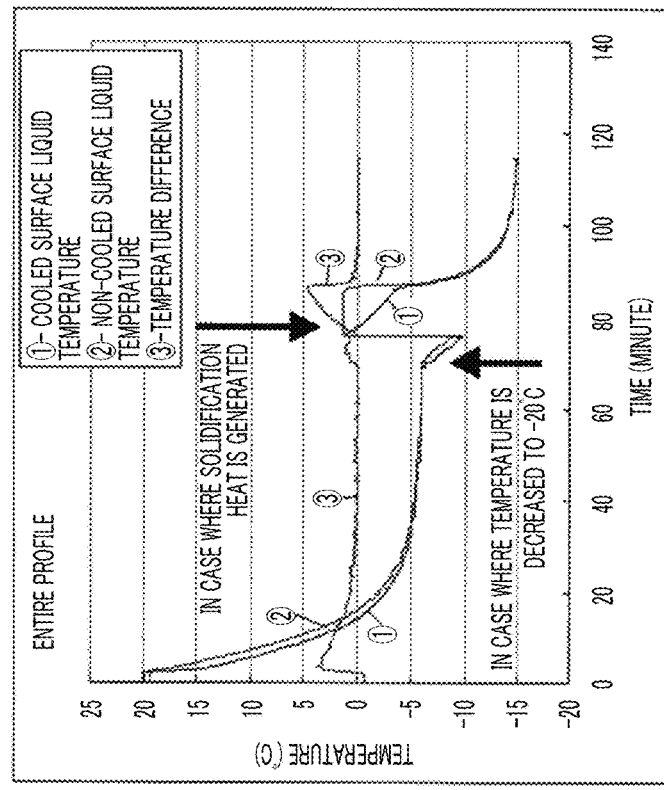

FIG. 3
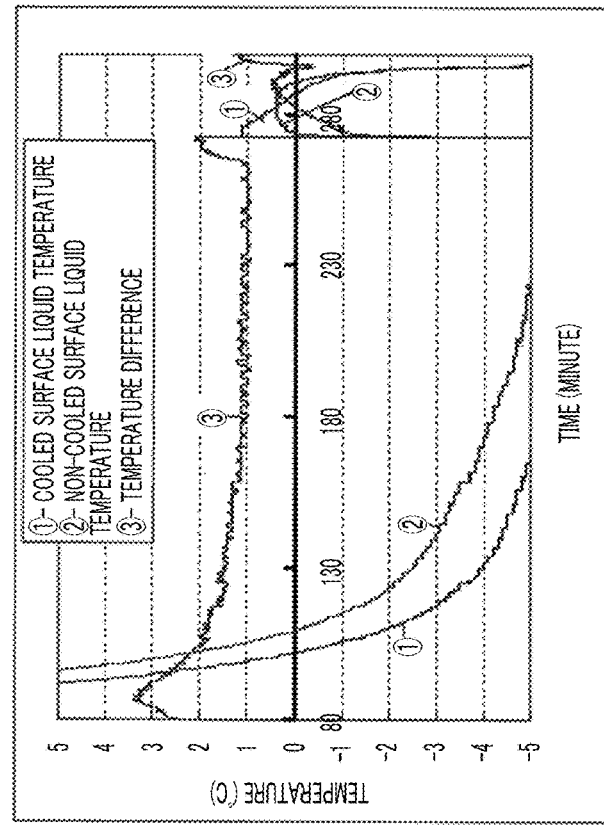
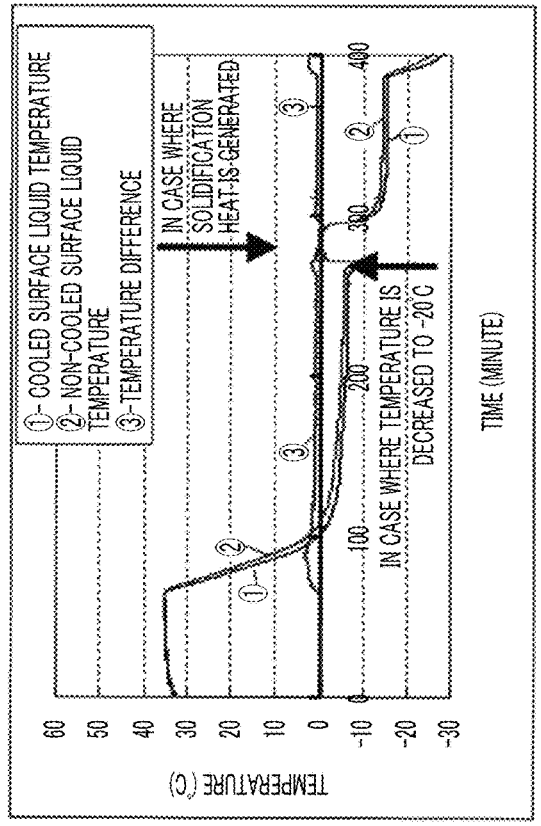

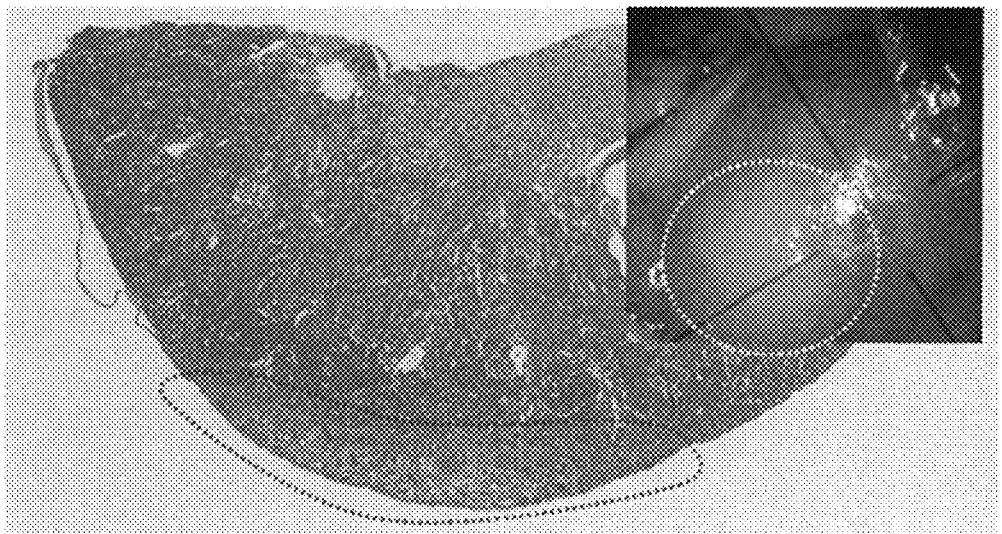
FIG. 14
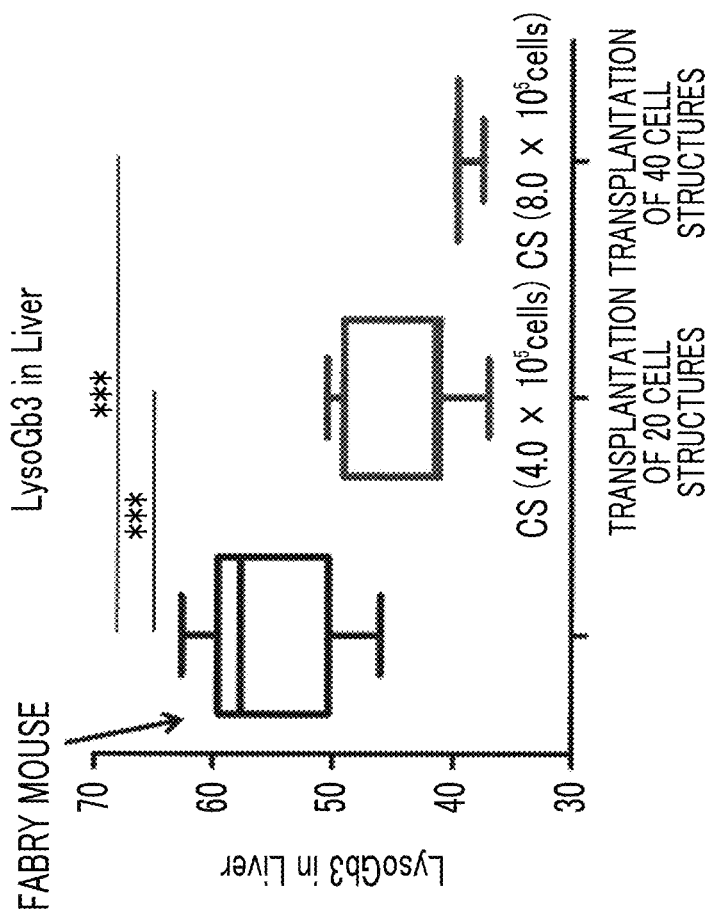

TREATMENT AGENT FOR LYSOSOMAL STORAGE DISEASE

CROSS-REFERENCE TO RELATED APPLICATIONS

This application is a Continuation of PCT International Application No. PCT/JP2018/024879 filed on Jun. 29, 2018, which claims priority under 35 U.S.C. § 119(a) to Japanese Patent Application No. 2017-128893 filed on Jun. 30, 2017. Each of the above application(s) is hereby expressly incorporated by reference, in its entirety, into the present application.

REFERENCE TO SEQUENCE LISTING SUBMITTED VIA EFS-WEB

This application includes an electronically submitted sequence listing in .txt format. The .txt file contains a sequence listing entitled "2870-0743PUS1_ST25.txt" created on Mar. 3, 2020 and is 31,912 bytes in size. The sequence listing contained in this .txt file is part of the specification and is hereby incorporated by reference herein in its entirety.

BACKGROUND OF THE INVENTION

1. Field of the Invention

The present invention relates to a treatment agent for a lysosomal storage disease, which includes a cell structure in which a plurality of polymer blocks are disposed in gaps between a plurality of cells.

2. Description of the Related Art

A lysosomal storage disease is a general term for diseases caused by accumulation of undecomposed substances in a lysosome, which is an intracellular organelle, due to a genetic abnormality which results in a deficiency in activity of one or more enzymes in a lysosome, or accumulation of substances in a lysosome due to dysfunction of a membrane protein in a lysosome. Lysosomal storage diseases are classified into a plurality of types according to individually abnormal enzymes or genes, and are intractable diseases with more than 60 types.

For the lysosomal storage disease, generally, an enzyme replacement therapy in which an enzyme is artificially replaced from outside of the body is performed. For example, the enzyme replacement therapy is performed for Fabry disease, but since a retention time of an enzyme preparation in the body is remarkably short, the enzyme preparation is required to be continuously administered over a lifetime at a frequency of once every two weeks, and thus a burden on a patient is large and Quality of Life (QOL) is low. Moreover, for some lysosomal storage diseases, enzyme preparations for the diseases are not present, and in this case, an effective therapeutic means is not present.

Furthermore, a technique of using a cell, in which a gene of an enzyme necessary for a therapy of a lysosomal storage disease is excessively expressed, for the therapy has also been developed. For example, JP4313381B discloses a cell for a therapy of α-galactosidase A deficiency, which is a human cell genetically modified to overexpress and secrete human α-gal A. U.S. Pat. No. 7,927,587B discloses that a stem cell such as a multipotent adult progenitor cell (MAPC) which is not subjected to gene transfer is used for a lysosomal storage disease.

WO2011/108517A discloses a cell structure which includes a polymer block having biocompatibility and a cell and in which a plurality of the polymer blocks are disposed in gaps between a plurality of the cells.

SUMMARY OF THE INVENTION

The use of the cell overexpressing the gene as disclosed in JP4313381B is not desirable also in view of harmfulness and danger to a living body. Moreover, in a case where the stem cell such as a multipotent adult progenitor cell (MAPC) is used alone as disclosed in U.S. Pat. No. 7,927,587B, the effect is not sustained and the stem cell cannot be used for the therapy. An object of the present invention is to provide an excellent treatment agent for a lysosomal storage disease.

As a result of intensive research to achieve the above object, the present inventors have found that a cell structure which includes a biocompatible polymer block and a cell and in which a plurality of the biocompatible polymer blocks are disposed in the gaps between a plurality of the cells is useful for treating a lysosomal storage disease, and completed the present invention.

That is, according to the present invention, the following inventions are provided.

<1> A treatment agent for a lysosomal storage disease, comprising a cell structure which includes a plurality of biocompatible polymer blocks and a plurality of cells of at least one type and in which at least one of the polymer blocks is disposed in gaps between the plurality of cells.

<2> The treatment agent described in <1>, in which the cells include at least a mesenchymal stem cell or a fibroblast.

<3> The treatment agent described in <1> or <2>, in which the cell structure includes 0.0000001 μg to 1 μg of the biocompatible polymer block per cell.

<4> The treatment agent described in any one of <1> to <3>, in which a size of each of the biocompatible polymer blocks is 10 μm to 300 μm.

<5> The treatment agent described in any one of <1> to <4>, in which a thickness or a diameter of the cell structure is 100 μm to 3 cm.

<6> The treatment agent described in any one of <1> to <5>, in which the biocompatible polymer block is formed of a recombinant peptide.

<7> The treatment agent described in <6>, in which the recombinant peptide is represented by the following formula.

Formula: A-[(Gly-X-Y)$_n$]$_m$-B

In the formula, A represents any amino acid or any amino acid sequence, B represents any amino acid or any amino acid sequence, n pieces of X each independently represent any amino acid, n pieces of Y each independently represent any amino acid, n represents an integer of 3 to 100, m represents an integer of 2 to 10, and n pieces of Gly-X-Y may be the same as or different from each other.

<8> The treatment agent described in <6> or <7>, in which the recombinant peptide is any one of a peptide which consists of an amino acid sequence described in SEQ ID NO: 1; a peptide which consists of an amino acid sequence in which one or several amino acids are deleted, substituted, or added in the amino acid sequence described in SEQ ID NO: 1, and has biocompatibility; or a peptide which consists of an amino acid sequence having 80% or more sequence identity with the amino acid sequence described in SEQ ID NO: 1, and has biocompatibility.

<9> The treatment agent described in any one of <1> to <8>, in which in the biocompatible polymer block, the biocompatible polymers are cross-linked by heat, an ultraviolet ray, or an enzyme.

<10> The treatment agent described in any one of <1> to <9>, in which the biocompatible polymer block is in a form of a granule obtained by pulverizing a porous body of the biocompatible polymer.

<11> The treatment agent described in any one of <1> to <10>, in which the lysosomal storage disease is Fabry disease.

<12> The treatment agent described in <11>, in which an amount of globotriaosylsphingosine in a living body is reduced by secreting α-galactosidase A in the living body.

Furthermore, according to the present invention, the following inventions are provided.

(A) A method of treating a lysosomal storage disease, comprising a step of transplanting a cell structure to a subject in need of a treatment for a lysosomal storage disease, the cell structure which includes a plurality of biocompatible polymer blocks and a plurality of cells of at least one type and in which at least one of the polymer blocks is disposed in gaps between the plurality of cells.

(B) A cell structure to be used in a treatment for a lysosomal storage disease, comprising a plurality of biocompatible polymer blocks and a plurality of cells of at least one type, in which at least one of the polymer blocks is disposed in gaps between the plurality of cells.

(C) Use of a cell structure for producing a treatment agent for a lysosomal storage disease, the cell structure which includes a plurality of biocompatible polymer blocks and a plurality of cells of at least one type and in which at least one of the polymer blocks is disposed in gaps between the plurality of cells.

The treatment agent of the present invention is useful as a treatment agent for a lysosomal storage disease.

BRIEF DESCRIPTION OF THE DRAWINGS

FIG. 1 illustrates a liquid temperature profiling of an experiment described in Condition A.

FIG. 2 illustrates a liquid temperature profiling of an experiment described in Condition B.

FIG. 3 illustrates a liquid temperature profiling of an experiment described in Condition C.

FIG. 14 illustrates results obtained by quantifying the amount of the LysoGb3 in the liver four weeks after the cell structure is transplanted under the renal capsule.

DESCRIPTION OF THE PREFERRED EMBODIMENTS

Figure 4:
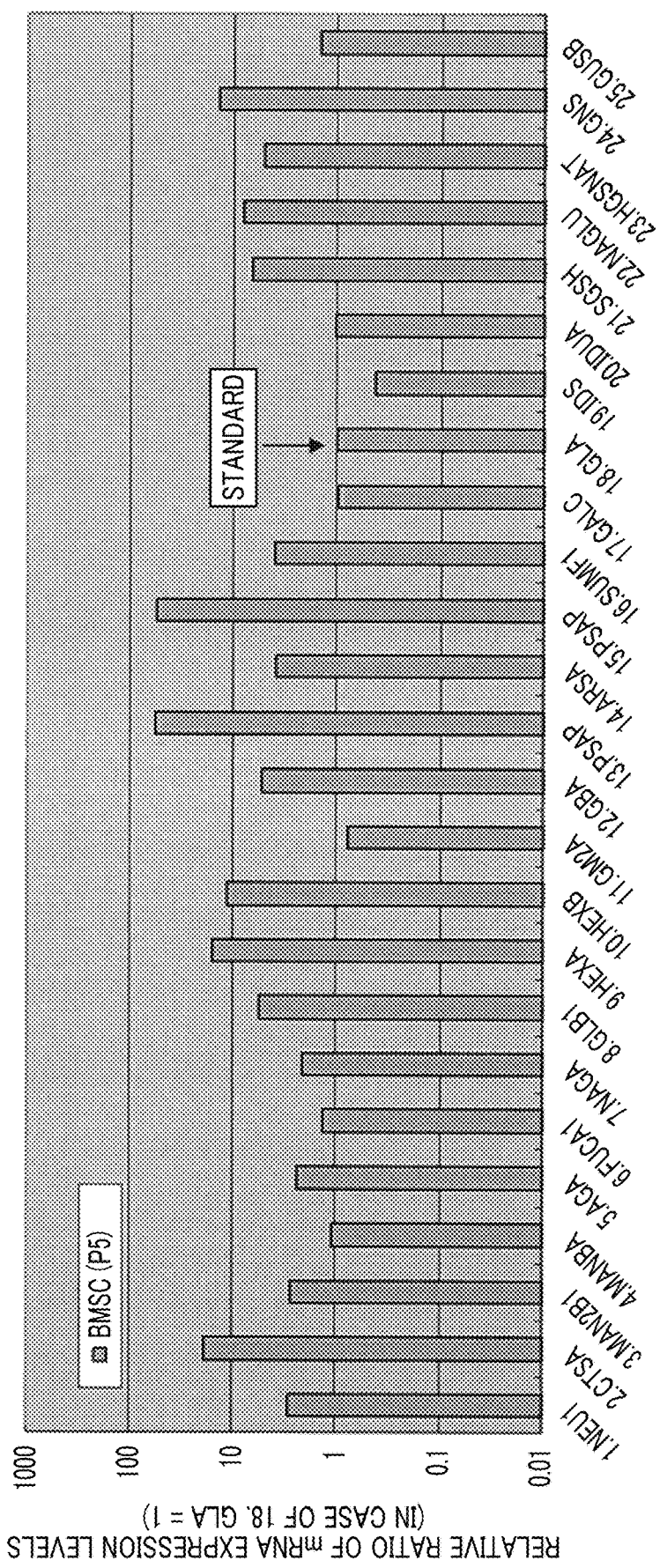
FIG. 4 illustrates expression levels of lysosomal storage disease-related enzymes in a human bone marrow-derived mesenchymal stem cell (hBMSC).
Figure 5:
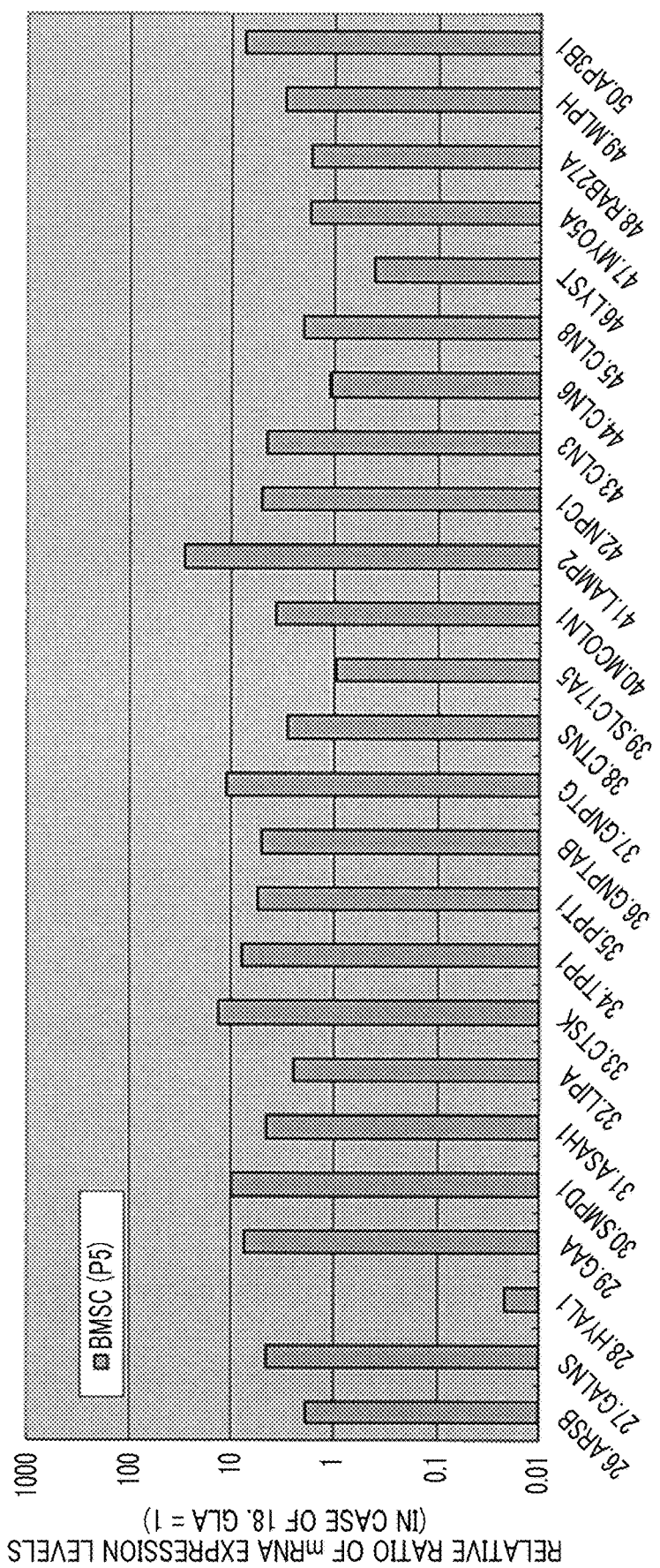
FIG. 5 illustrates expression levels of lysosomal storage disease-related enzymes in a human bone marrow-derived mesenchymal stem cell (hBMSC).
Figure 6:
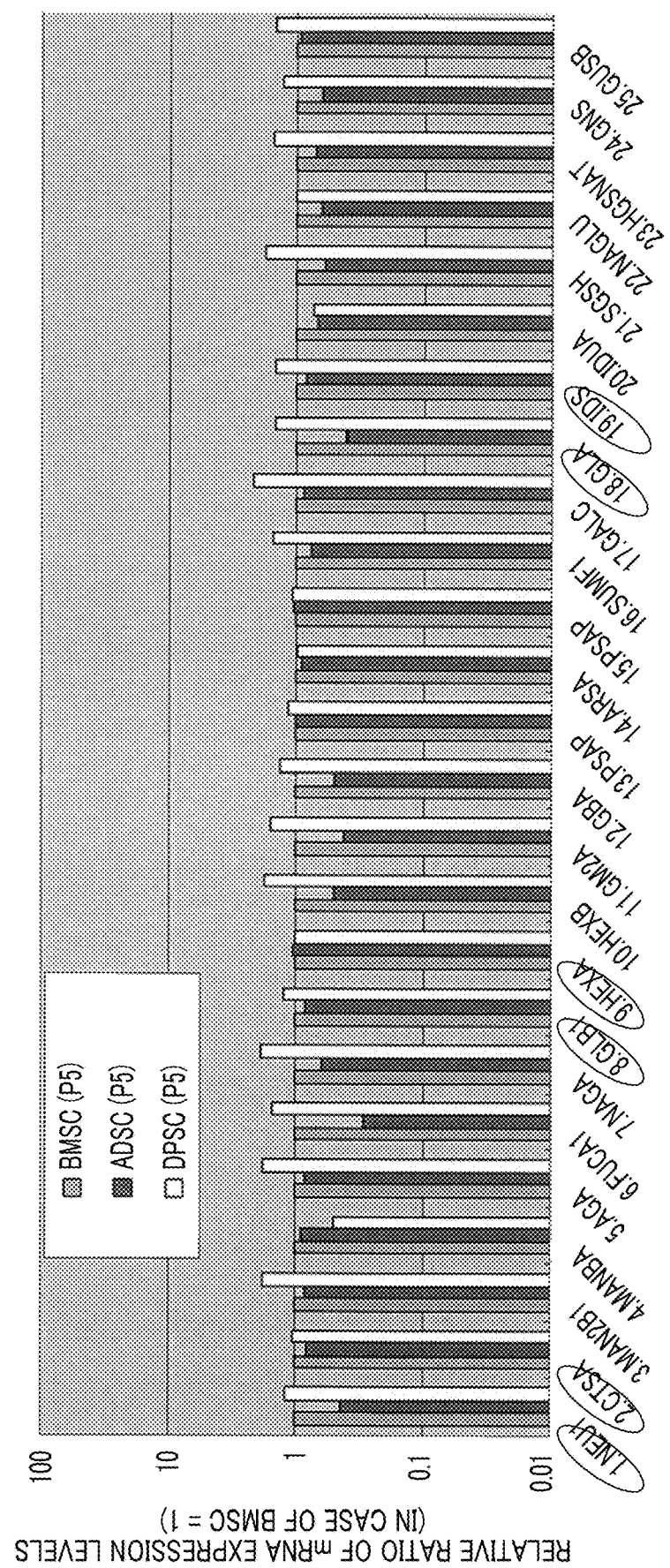
FIG. 6 illustrates expression levels of lysosomal storage disease-related enzymes in the human bone marrow-derived mesenchymal stem cell (hBMSC), a human adipose-derived stem cell (hADSC), and a human dental pulp-derived stem cell (hDPSC). Enzyme preparations for NEU1, CTSA, GLB1, and HEXA have not yet been developed, and the enzymes correspond to the top six types with a large number of patients. IDS is one type with the largest number of patients.
Figure 7:
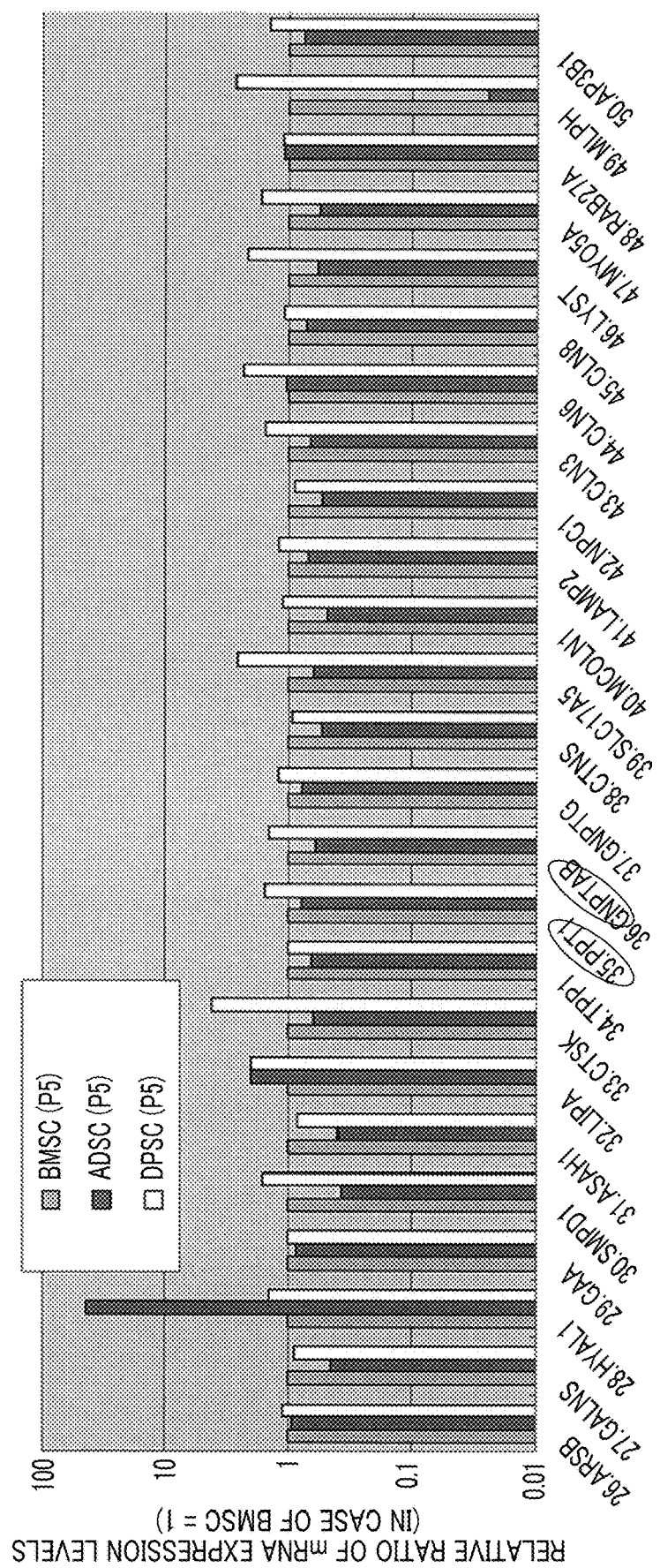
FIG. 7 illustrates expression levels of lysosomal storage disease-related enzymes in the human bone marrow-derived mesenchymal stem cell (hBMSC), the human adipose-derived stem cell (hADSC), and the human dental pulp-derived stem cell (hDPSC). Enzyme preparations for PPTI and GNPTAB have not yet been developed, and the enzymes correspond to the top six types with a large number of patients.

Hereinafter, embodiments for implementing the present invention are specifically described.

In the present specification, a cell structure used in the present invention is referred to as a mosaic cell cluster (cell cluster formed in a mosaic shape) in some cases. The expression "to" in the present specification refers to a range including numerical values described before and after the expression as a minimum value and a maximum value, respectively.

The present invention relates to a treatment agent for a lysosomal storage disease including a cell structure which includes a plurality of biocompatible polymer blocks and a plurality of cells of at least one type and in which at least one of the polymer blocks is disposed in gaps between the plurality of cells. According to the treatment agent for a lysosomal storage disease according to the embodiment of the present invention, treatment effects can be continuously maintained.

As shown in the following examples, it was found that in a group in which a cell structure was administered to a mouse with Fabry disease, an amount of LysoGb3 in a liver was significantly reduced, compared with a group in which the cell structure was not administered and a group in which only a cell was administered. From the results shown in the examples, it is clarified that in a case where a cell is administered as a cell structure, high effectiveness for a mouse with Fabry disease is exhibited, which is a totally unexpected effect.

(1) Biocompatible Polymer Block (1-1) Biocompatible Polymer

Biocompatibility means that a remarkable adverse reaction such as a long-term and chronic inflammatory reaction is not caused upon contact with a living body. Regarding the biocompatible polymer used in the present invention, whether to be decomposed within a living body is not particularly limited as long as the biocompatible polymer has an affinity for the living body. However, a biodegradable polymer is preferable. Specific examples of a non-biodegradable material include polytetrafluoroethylene (PTFE), polyurethane, polypropylene, polyester, vinyl chloride, polycarbonate, acryl, stainless steel, titanium, silicone, and 2-methacryloyloxyethyl phosphorylcholine (MPC). Specific examples of a biodegradable material include a polypeptide (for example, gelatin described below) such as a naturally occurring peptide, a recombinant peptide, or a chemically synthesized peptide, polylactic acid, polyglycolic acid, poly (lactic-co-glycolic acid) (PLGA), hyaluronic acid, glycosaminoglycan, proteoglycan, chondroitin, cellulose, agarose, carboxymethyl cellulose, chitin, and chitosan. Among these, a recombinant peptide is particularly preferable. The biocompatible polymers may be devised to improve cell adhesiveness. Specifically, a method such as "coating a substrate surface with cell adhesion stroma (fibronectin, vitronectin, or laminin) or a peptide having cell adhesion sequence (an RGD sequence, an LDV sequence, an REDV sequence (SEQ ID NO: 2), a YIGSR sequence (SEQ ID NO: 3), a PDSGR sequence (SEQ ID NO: 4), an RYVVLPR sequence (SEQ ID NO: 5), an LGTIPG sequence (SEQ ID NO: 6), an RNIAEIIKDI sequence (SEQ ID NO: 7), an IKVAV sequence (SEQ ID NO: 8), an LRE sequence, a DGEA sequence (SEQ ID NO: 9), and a HAV sequence, all expressed as one letter code of amino acids)", "amination and cationization of a substrate surface", or "a plasma treatment and a hydrophilic treatment due to corona discharge on a substrate surface" can be used.

The type of a polypeptide including a recombinant peptide or a chemically synthesized peptide is not particularly limited as long as the polypeptide has biocompatibility. For example, gelatin, collagen, atelocollagen, elastin, fibronectin, pronectin, laminin, tenascin, fibrin, fibroin, entactin, thrombospondin, and RETRONECTIN (registered trademark) are preferable, and gelatin, collagen, and atelocollagen are most preferable. Gelatin to be used in the present invention is preferably natural gelatin, recombinant gelatin, or chemically synthesized gelatin, and more preferably recombinant gelatin. The natural gelatin referred to herein means gelatin produced using naturally derived collagen.

The chemically synthesized peptide and the chemically synthesized gelatin mean an artificially synthesized peptide and artificially synthesized gelatin, respectively. A peptide such as gelatin may be synthesized by solid phase synthesis or liquid phase synthesis, but the solid phase synthesis is preferable. The solid phase synthesis of the peptide is well-known to those skilled in the art, and examples thereof include a fluorenyl-methoxy-carbonyl group (Fmoc group) synthesis method in which a Fmoc group is used for protection of an amino group, and a tert-butyl oxy carbonyl group (Boc group) synthesis method in which a Boc group is used for protection of an amino group. As the preferred embodiment of the chemically synthesized gelatin, the contents described in the recombinant gelatin described below in the present specification can be applied.

A "1/IOB" value which is a hydrophilicity value of the biocompatible polymer used in the present invention is preferably 0 to 1.0. The 1/IOB value is more preferably 0 to 0.6 and still more preferably 0 to 0.4. IOB is an index of hydrophilicity and hydrophobicity based on an organic conceptual diagram showing polarity and non-polarity of an organic compound, which has been proposed by Atsushi FUJITA, and the details thereof are described in, for example, "Pharmaceutical Bulletin", Vol. 2, 2, pp. 163 to 173 (1954), "Area of Chemistry", Vol. 11, 10, pp. 719 to 725 (1957), and "Fragrance Journal", Vol. 50, pp. 79 to 82 (1981). Briefly, assuming that the source of all organic compounds is methane ($CH_4$) and all other compounds are derivatives of methane, predetermined numerical values are set for the number of carbons, a substituent, a transformation portion, a ring, and the like of the compounds, scores thereof are added to determine an organic value (OV) and an inorganic value (IV), and these values are plotted on a diagram in which the organic value is placed on an X-axis and the inorganic value is placed on a Y-axis. IOB in the organic conceptual diagram refers to a ratio of the inorganic value (IV) to the organic value (OV) in the organic conceptual diagram, that is, "inorganic value (IV)/organic value (OV)". For the details of the organic conceptual diagram, "New Edition Organic Conceptual Diagram-Foundation and Application" (written by Yoshio KOUDA et al., Sankyo Shuppan Co., Ltd., 2008) can be referred to. In the present specification, the hydrophilicity and hydrophobicity are represented by a "1/IOB" value obtained by taking a reciprocal of IOB. A smaller "1/IOB" value (close to 0) indicates higher hydrophilicity.

It is presumed that since hydrophilicity becomes high and water absorbency becomes high by setting the "1/IOB" value of the polymer used in the present invention in the above range, the polymer effectively acts to retain nutrient components and, as a result, contributes to the stabilization and viability of cells in the cell structure (mosaic cell cluster) according to the present invention.

In a case where the biocompatible polymer used in the present invention is a polypeptide, the hydrophilicity and hydrophobicity index represented by a grand average of hydropathicity (GRAVY) value is preferably −9.0 to 0.3 and more preferably −7.0 to 0.0. The grand average of hydropathicity (GRAVY) value can be obtained by methods of "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571 to 607" and "Gasteiger E., Gattiker A., Hoogland C., Ivanyi I., Appel R. D., Bairoch A.; ExPASy: the proteomics server for in-depth protein knowledge and analysis.; Nucleic Acids Res. 31:3784-3788 (2003)".

It is presumed that since hydrophilicity becomes high and water absorbency becomes high by setting the GRAVY value of the polymer used in the present invention in the above range, the polymer effectively acts to retain nutrient components and, as a result, contributes to the stabilization and viability of cells in the cell structure (mosaic cell cluster) according to the present invention.

(1-2) Cross-Linking

The biocompatible polymers used in the present invention may be or may not be cross-linked, but are preferably cross-linked. By using the cross-linked biocompatible polymers, it is possible to obtain an effect of preventing instant decomposition thereof at the time of culturing in a medium and at the time of transplantation into a living body. As general cross-linking methods, thermal cross-linking, cross-linking using aldehydes (for example, formaldehyde, glutaraldehyde, or the like), cross-linking using a condensation agent (carbodiimide, cyanamide, or the like), enzymatic cross-linking, photo cross-linking, ultraviolet cross-linking, a hydrophobic interaction, hydrogen bonding, an ionic interaction, and the like are known, and the cross-linking methods can be used in the present invention. As the cross-linking methods used in the present invention, thermal cross-linking, ultraviolet cross-linking, or enzymatic cross-linking is more preferable, and thermal cross-linking is particularly preferable.

In a case of performing cross-linking using an enzyme, the enzyme is not particularly limited as long as the enzyme has a function of cross-linking polymer materials. However, it is possible to perform cross-linking preferably using transglutaminase and laccase, and most preferably using transglutaminase. Specific examples of proteins which are enzymatically cross-linked by transglutaminase are not particularly limited as long as the proteins have a lysine residue and a glutamine residue. Transglutaminase may be derived from a mammal or a microorganism. Specific examples thereof include ACTIVA series manufactured by Ajinomoto Co., Inc., mammal-derived transglutaminase which is sold as a reagent, for example, guinea pig liver-derived transglutaminase, goat-derived transglutaminase, and rabbit-derived transglutaminase, which are manufactured by Oriental Yeast Co., Ltd., Upstate USA Inc., and Biodesign International Inc., and human-derived blood coagulation factor (Factor XIIIa, Haematologic Technologies, Inc.).

The reaction temperature in a case of performing cross-linking (for example, thermal cross-linking) is not particularly limited as long as cross-linking can be performed, but is preferably −100° C. to 500° C., more preferably 0° C. to 300° C., still more preferably 50° C. to 300° C., particularly preferably 100° C. to 250° C., and most preferably 120° C. to 200° C.

(1-3) Recombinant Gelatin

The recombinant gelatin referred to in the present invention means a polypeptide or a protein-like substance which is produced by gene recombination technology and has an amino acid sequence similar to that of gelatin. The recombinant gelatin which can be used in the present invention preferably has repetition of a sequence represented by Gly-X-Y (X and Y each independently represent any amino acid) which is characteristic of collagen. Herein, a plurality of pieces of Gly-X-Y may be the same as or different from each other. Preferably, two or more sequences of cell adhesion signals are included in one molecule. As the recombinant gelatin used in the present invention, it is possible to use recombinant gelatin having an amino acid sequence derived from a partial amino acid sequence of collagen. For example, it is possible to use recombinant gelatin disclosed in EP1014176, U.S. Pat. No. 6,992,172B, WO2004/085473A, and WO2008/103041A, but the present invention is not limited thereto. A preferred example of the recombinant gelatin used in the present invention is recombinant gelatin of the following aspect.

The recombinant gelatin is excellent in biocompatibility due to original characteristics of natural gelatin, is not naturally derived so that there is no concern about bovine spongiform encephalopathy (BSE) or the like, and is excellent in non-infection properties. The recombinant gelatin is more uniform than natural gelatin, and a sequence thereof is determined. Accordingly, it is possible to precisely design the strength and degradability with less fluctuation due to cross-linking or the like.

The molecular weight of the recombinant gelatin is not particularly limited, and is preferably 2,000 to 100,000 (2 kilodaltons (kDa) to 100 kDa), more preferably 2,500 to 95,000 (2.5 kDa to 95 kDa), still more preferably 5,000 to 90,000 (5 kDa to 90 kDa), and most preferably 10,000 to 90,000 (10 kDa to 90 kDa).

The recombinant gelatin preferably has repetition of a sequence represented by Gly-X-Y which is characteristic of collagen. Herein, a plurality of pieces of Gly-X-Y may be the same as or different from each other. In Gly-X-Y, Gly represents glycine and X and Y represent any amino acid (preferably represents any amino acid other than glycine). The sequence represented by Gly-X-Y which is characteristic of collagen is a partial structure which is extremely specific in a sequence and a composition of an amino acid of gelatin and collagen, compared with other proteins. In this portion, glycine occupies about one third of the entire sequence, and is repeated at every third position in an amino acid sequence. Glycine is the simplest amino acid, has little restraint on the arrangement of the molecular chains, and significantly contributes to regeneration of a helix structure during gelation. It is preferable that amino acids represented by X and Y contain many imino acids (proline and oxyproline) and occupy 10% to 45% of the entire sequence. Preferably 80% or more, more preferably 95% or more, and most preferably 99% or more of the amino acids in the sequence of the recombinant gelatin have a repeating structure of Gly-X-Y.

In general gelatin, a polar charged amino acid and a polar uncharged amino acid are present at a ratio of 1:1. Herein, the polar amino acid specifically indicates cysteine, aspartic acid, glutamic acid, histidine, lysine, asparagine, glutamine, serine, threonine, tyrosine, and arginine. Among these, the polar uncharged amino acid indicates cysteine, asparagine, glutamine, serine, threonine, and tyrosine. In the recombinant gelatin used in the present invention, the proportion of the polar amino acid in the whole constituent amino acid is 10% to 40% and is preferably 20% to 30%. The proportion of the uncharged amino acid in the polar amino acids is greater than or equal to 5% and less than 20% and is preferably greater than or equal to 5% and less than 10%. It is preferable that any one amino acid or preferably two or more amino acids among serine, threonine, asparagine, tyrosine, and cysteine are not contained on the sequence.

In general, a minimum amino acid sequence which functions as a cell adhesion signal in a polypeptide is known (for example, Nagai Shoten Co., Ltd., "Pathophysiology", Vol. 9, No. 7 (1990), p. 527). The recombinant gelatin used in the present invention preferably has two or more cell adhesion signals in one molecule. As the specific sequence, sequences such as an RGD sequence, an LDV sequence, an REDV sequence (SEQ ID NO: 2), a YIGSR sequence (SEQ ID NO: 3), a PDSGR sequence (SEQ ID NO: 4), an RYVVLPR sequence (SEQ ID NO: 5), an LGTIPG sequence (SEQ ID NO: 6), an RNIAEIIKDI sequence (SEQ ID NO: 7), an IKVAV sequence (SEQ ID NO: 8), an LRE sequence, a DGEA sequence (SEQ ID NO: 9), and a HAV sequence, which are expressed as one letter code of amino acids, are preferable because many kinds of cells adhere to these sequences. An RGD sequence, a YIGSR sequence (SEQ ID NO: 3), a PDSGR sequence (SEQ ID NO: 4), an LGTIPG sequence (SEQ ID NO: 6), an IKVAV sequence (SEQ ID NO: 8), and a HAV sequence are more preferable, and an RGD sequence is particularly preferable. In the RGD sequences, an ERGD sequence (SEQ ID NO: 10) is preferable. A production amount of stroma of a cell can be improved by using recombinant gelatin having cell adhesion signals.

As the disposition of RGD sequences in the recombinant gelatin used in the present invention, it is preferable that the number of amino acids between RGDs is not uniform between 0 and 100, and it is more preferable that the number of amino acids between RGDs is not uniform between 25 and 60.

The content of this minimum amino acid sequence unit is preferably 3 to 50, more preferably 4 to 30, particularly preferably 5 to 20, and most preferably 12 in one molecule of a protein in view of cell adhesion and proliferation properties.

In the recombinant gelatin used in the present invention, a proportion of an RGD motif with respect to the total number of amino acids is preferably at least 0.4%. In a case where the recombinant gelatin contains 350 or more amino acids, each stretch of the 350 amino acids preferably contains at least one RGD motif. The proportion of the RGD motif with respect to the total number of amino acids is more preferably at least 0.6%, still more preferably at least 0.8%, even more preferably at least 1.0%, particularly preferably at least 1.2%, and most preferably at least 1.5%. The number of RGD motifs within a recombinant peptide is preferably at least 4, more preferably at least 6, still more preferably at least 8, and particularly preferably 12 to 16 per 250 amino acids. The proportion of the RGD motif of 0.4% corresponds to at least one RGD sequence per 250 amino acids. The number of RGD motifs is an integer, and accordingly, gelatin consisting of 251 amino acids needs to contain at least two RGD sequences in order to satisfy the characteristics of 0.4%. The recombinant gelatin of the present invention preferably contains at least two RGD sequences per 250 amino acids, more preferably contains at least three RGD sequences per 250 amino acids, and still more preferably contains at least four RGD sequences per 250 amino acids. As another aspect of the recombinant gelatin of the present invention, the recombinant gelatin preferably contains at least 4 RGD motifs, more preferably contains at least 6 RGD motifs, still more preferably contains at least 8 RGD motifs, and particularly preferably contains 12 to 16 RGD motifs.

The recombinant gelatin may be partially hydrolyzed.

The recombinant gelatin used in the present invention is preferably represented by Formula of A-[(Gly-X-Y)$_n$]$_m$-B. n pieces of X each independently represent any amino acid and n pieces of Y each independently represent any amino acid. m preferably represents an integer of 2 to 10 and more preferably represents an integer of 3 to 5. n is preferably an integer of 3 to 100, more preferably an integer of 15 to 70, and most preferably an integer of 50 to 65. A represents any amino acid or any amino acid sequence and B represents any amino acid or any amino acid sequence. n pieces of Gly-X-Y may be the same as or different from each other.

More preferably, the recombinant gelatin used in the present invention is represented by Gly-Ala-Pro-[(Gly-X-Y)$_{63}$]$_3$-Gly (SEQ ID NO: 11) (in the formula, 63 pieces of X each independently represent any amino acid and 63 pieces of Y each independently represent any amino acid. 63 pieces of Gly-X-Y may be the same as or different from each other).

It is preferable that a plurality of sequence units of naturally existing collagen are bonded to a repeating unit. The naturally existing collagen referred to herein is not limited as long as the collagen exists naturally, but is preferably I type collagen, II type collagen, III type collagen, IV type collagen, or V type collagen, and more preferably I type collagen, II type collagen, or III type collagen. According to another embodiment, the above-described collagen is derived preferably from a human, cattle, a pig, a mouse, or a rat, and more preferably from a human.

An isoelectric point of the recombinant gelatin used in the present invention is preferably 5 to 10, more preferably 6 to 10, and still more preferably 7 to 9.5. The measurement of the isoelectric point of the recombinant gelatin can be carried out by measuring a pH after passing a 1 mass % gelatin solution through a mixed crystal column of a cation-anion exchange resin, as described in the isoelectric focusing method (refer to Maxey, C. R. (1976); Phitogr. Gelatin 2, Editor Cox, P. J. Academic, London, Engl.).

It is preferable that the recombinant gelatin is not deaminated.

It is preferable that the recombinant gelatin does not have a telopeptide.

It is preferable that the recombinant gelatin is a substantially pure polypeptide prepared using a nucleic acid which encodes an amino acid sequence.

It is particularly preferable that the recombinant gelatin used in the present invention is any of (1) a peptide consisting of an amino acid sequence described in SEQ ID NO: 1;

(2) a peptide which consists of an amino acid sequence in which one or several amino acids are deleted, substituted, or added in the amino acid sequence described in SEQ ID NO: 1, and has biocompatibility; or (3) a peptide which consists of an amino acid sequence having 80% or more (more preferably 90% or more, particularly preferably 95% or more, and most preferably 98% or more) sequence identity with the amino acid sequence described in SEQ ID NO: 1, and has biocompatibility.

The sequence identity in the present invention refers to a value calculated by the following expression.

% Sequence identity=[(the number of identical residues)/(alignment length)]×100

The sequence identity between two amino acid sequences can be determined by any method well-known to those skilled in the art, and can be determined by using a basic local alignment search tool (BLAST) program (J. Mol. Biol. 215: 403 to 410, 1990) or the like.

"One or several" in the expression "amino acid sequence in which one or several amino acids are deleted, substituted, or added" means preferably 1 to 20 amino acids, more preferably 1 to 10 amino acids, still more preferably 1 to 5 amino acids, and particularly preferably 1 to 3 amino acids.

The recombinant gelatin used in the present invention can be produced by a gene recombination technology which is well-known to those skilled in the art, and can be produced, for example, in accordance with methods disclosed in EP1014176A2, U.S. Pat. No. 6,992,172B, WO2004/085473A, and WO2008/103041A. Specifically, a gene encoding an amino acid sequence of predetermined recombinant gelatin is acquired, the acquired gene is incorporated into an expression vector to produce a recombinant expression vector, and a transformant is produced by introducing the recombinant expression vector into an appropriate host. The recombinant gelatin is produced by culturing the obtained transformant in an appropriate medium. Accordingly, the recombinant gelatin used in the present invention can be prepared by collecting the recombinant gelatin produced from a culture product.

(1-4) Biocompatible Polymer Block

In the present invention, a block (cluster) formed of the above-described biocompatible polymers is used.

The shape of the biocompatible polymer block in the present invention is not particularly limited. Examples thereof include an amorphous shape, a spherical shape, a particulate shape (granule), a powdery shape, a porous shape, a fibrous shape, a spindle shape, a flat shape, and a sheet shape, and an amorphous shape, a spherical shape, a particulate shape (granule), a powdery shape, and a porous shape are preferable. The amorphous shape indicates that a shape of a surface is uneven, and indicates, for example, an object having roughness, such as rock. Examples of the above-described shapes are not distinct from each other, and, for example, an amorphous shape is included in an example of a subordinate concept of the particulate shape (granule) in some cases.

The shape of the biocompatible polymer block in the present invention is not particularly limited as described above. However, tap density is preferably 10 mg/cm$^3$ to 500 mg/cm$^3$, more preferably 20 mg/cm$^3$ to 400 mg/cm$^3$, still more preferably 40 mg/cm$^3$ to 220 mg/cm$^3$, and particularly preferably 50 mg/cm$^3$ to 150 mg/cm$^3$.

The tap density is a value indicating how many blocks can be densely packed in a certain volume, and it is apparent that as the value becomes lower, the blocks cannot be densely packed, that is, the structure of the block is complicated. It is considered that the tap density of the biocompatible polymer block indicates complexity of a surface structure of the biocompatible polymer block and a volume of a void formed in a case where biocompatible polymer blocks are collected as an aggregate. As the tap density becomes smaller, the void between biocompatible polymer blocks becomes larger and a grafted region of a cell becomes larger. In addition, by setting the tap density to be not too small, the biocompatible polymer block can appropriately exist between cells, and in a case where a cell structure is formed, nutrients can be delivered into the cell structure. Therefore, it is considered to be preferable that the tap density falls within the above range.

The measurement of the tap density referred to in the present specification is not particularly limited, but can be performed as follows. A container (having a cylindrical shape with a diameter of 6 mm and a length of 21.8 mm: a capacity of 0.616 cm$^3$) (hereinafter, described as a cap) is prepared for the measurement. First, a mass of only the cap is measured. Then, a funnel is attached to the cap, and blocks are poured from the funnel so as to be accumulated in the cap. After pouring a sufficient amount of blocks, the cap portion is hit 200 times on a hard object such as a desk, the funnel is removed, and the blocks are leveled off with a spatula. A mass is measured in a state where the cap is filled up with the blocks. The tap density can be determined by calculating a mass of only the blocks from the difference between the mass of the cap filled up with the blocks and the mass of only the cap, and dividing the mass of only the blocks by the volume of the cap.

A cross-linking degree of the biocompatible polymer block in the present invention is not particularly limited, but is preferably greater than or equal to 2, more preferably 2 to 30, still more preferably 4 to 25, and particularly preferably 4 to 22.

The method of measuring the cross-linking degree (the number of times of cross-linking per molecule) of the biocompatible polymer block is not particularly limited. However, in a case where the biocompatible polymer is CBE3, the measurement can be performed, for example, by a TNBS (2,4,6-trinitrobenzene sulfonic acid) method described in the following examples. Specifically, a sample obtained by mixing a biocompatible polymer block, a NaHCO$_3$ aqueous solution, and a TNBS aqueous solution, allowing the mixture to react for 3 hours at 37° C., and then stopping the reaction, and a blank obtained by mixing a biocompatible polymer block, a NaHCO$_3$ aqueous solution, and a TNBS aqueous solution and stopping a reaction immediately after the mixing are prepared. Each absorbance (345 nm) of the sample and the blank which are diluted with pure water is measured, and the cross-linking degree (the number of times of cross-linking per molecule) can be calculated from (Expression 2) and (Expression 3).

$$(As-Ab)/14{,}600 \times V/w \quad \text{(Expression 2)}$$

(Expression 2) represents an amount (molar equivalent) of lysine per 1 g of the biocompatible polymer block.

(In the expression, As represents a sample absorbance, Ab represents a blank absorbance, V represents an amount (g) of reaction liquid, and w represents a mass (mg) of the biocompatible polymer block.)

$$1-(\text{sample(Expression 2)/uncross-linked polymer (Expression 2)}) \times 34 \quad \text{(Expression 3)}$$

(Expression 3) represents the number of times of cross-linking per molecule.

A water absorption rate of the biocompatible polymer block in the present invention is not particularly limited, but is preferably greater than or equal to 300%, more preferably greater than or equal to 400%, still more preferably greater than or equal to 500%, particularly preferably greater than or equal to 600%, and most preferably greater than or equal to 700%. An upper limit of the water absorption rate is not particularly limited, but is generally less than or equal to 4,000% or less than or equal to 2,000%.

The method of measuring the water absorption rate of the biocompatible polymer block is not particularly limited. However, the water absorption rate can be measured, for example, by the method described in the following examples. Specifically, a 3 cm×3 cm bag made of nylon mesh is filled with about 15 mg of a biocompatible polymer block at 25° C., is swollen in ion exchange water for 2 hours, and then is dried with air for 10 minutes, the mass thereof is measured at each stage, the water absorption rate is determined according to (Expression 4).

$$\text{Water absorption rate}=(w2-w1-w0)/w0 \quad \text{(Expression 4)}$$

(In the expression, w0 represents a mass of a material before water absorption, w1 represents a mass of an empty bag after water absorption, and w2 represents a mass of a whole bag containing the material after water absorption.)

The size of one biocompatible polymer block in the present invention is not particularly limited, but is preferably 20 μm to 200 μm, more preferably 20 μm to 150 μm, still more preferably 50 μm to 120 μm, and particularly preferably 53 μm to 106 μm.

By setting the size of one biocompatible polymer block in the above range, nutrient delivery into a cell structure from the outside can be improved. The size of one biocompatible polymer block does not mean that an average value of the sizes of a plurality of biocompatible polymer blocks is within the above range, but means the size of each biocompatible polymer block which is obtained by sieving a plurality of biocompatible polymer blocks.

The size of one block can be defined by a size of a sieve used in a case of dividing the blocks. For example, blocks remaining on a sieve with 106 μm in a case where blocks which have been passed through a sieve with 180 μm for sifting are sifted using the sieve with 106 μm can be regarded as blocks having a size of 106 to 180 μm. Next, blocks remaining on a sieve with 53 μm in a case where blocks which have been passed through the sieve with 106

μm for sifting are sifted using the sieve with 53 μm can be regarded as blocks having a size of 53 to 106 μm. Next, blocks remaining on a sieve with 25 μm in a case where blocks which have been passed through the sieve with 53 μm for sifting are sifted using the sieve with 25 μm can be regarded as blocks having a size of 25 to 53 μm.

(1-5) Method of Producing Biocompatible Polymer Block

The method of producing a biocompatible polymer block is not particularly limited. For example, it is possible to obtain a biocompatible polymer block by pulverizing a solid matter (such as a porous body of a biocompatible polymer) containing a biocompatible polymer using a pulverizer (such as NEW POWER MILL). The solid matter (such as a porous body) containing a biocompatible polymer can be obtained, for example, by freeze-drying an aqueous solution containing the biocompatible polymer.

By pulverizing the solid matter containing a biocompatible polymer as described above, an amorphous biocompatible polymer block having an uneven surface shape can be produced.

The method of producing the porous body of the biocompatible polymer is not particularly limited, but the porous body can also be obtained by freeze-drying an aqueous solution containing a biocompatible polymer. For example, by including a freezing step in which the liquid temperature (highest internal highest liquid temperature) of a portion having the highest liquid temperature in the solution is lower than or equal to "solvent melting point −3° C." in the unfrozen state, the ice to be formed can have a spherical shape. By drying the ice after performing this step, a porous body having spherical isotropic holes (spherical pores) can be obtained. For example, by performing freezing without including a freezing step in which the liquid temperature (highest internal liquid temperature) of a portion having the highest liquid temperature in the solution is higher than or equal to "solvent melting point −3° C." in the unfrozen state, the ice to be formed can have a pillar/flat plate shape. By drying the ice after performing this step, a porous body having holes (pillars/flat plate pores) with pillar or flat shapes which are long uniaxially or biaxially can be obtained. In a case where the porous body of the biocompatible polymer is pulverized to produce a biocompatible polymer block, the holes of the porous body before pulverization influence the shape of the biocompatible polymer block to be obtained, and thus the shape of the biocompatible polymer block to be obtained can be adjusted by adjusting the condition of freeze-drying as described above.

An example of a method of producing a porous body of a biocompatible polymer includes a method including:

a step (a) of cooling a solution of biocompatible polymers to an unfrozen state under the conditions where the difference between a temperature of a portion having the highest liquid temperature in the solution and a temperature of a portion having the lowest liquid temperature in the solution is lower than or equal to 2.5° C. and the temperature of the portion having the highest liquid temperature in the solution is lower than or equal to a melting point of a solvent;

a step (b) of freezing the solution of the biocompatible polymers obtained in the step (a); and a step (c) of freeze-drying the frozen biocompatible polymers obtained in the step (b). However, the present invention is not limited to the above method.

In a case where the solution of the biocompatible polymers is cooled to an unfrozen state, the variation in the sizes of obtained porous pores is reduced by making the difference between the temperature of the portion having the highest liquid temperature and the temperature of the portion having the lowest liquid temperature in the solution be lower than or equal to 2.5° C. (preferably lower than or equal to 2.3° C. and more preferably lower than or equal to 2.1° C.), that is, by reducing the difference in temperature. A lower limit of the difference between the temperature of the portion having the highest liquid temperature and the temperature of the portion having the lowest liquid temperature in the solution is not particularly limited, but may be higher than or equal to 0° C. For example, the lower limit thereof may be higher than or equal to 0.1° C., higher than or equal to 0.5° C., higher than or equal to 0.8° C., or higher than or equal to 0.9° C. Accordingly, the cell structure using the biocompatible polymer block which is produced with the produced porous body achieves the effect of showing a large number of cells.

The cooling in the step (a) is preferably carried out, for example, using a material (preferably TEFLON (registered trademark)) having a lower thermal conductivity than water. The portion having the highest liquid temperature in the solution can be supposed as the farthest portion from a cooling side, and the portion having the lowest liquid temperature in the solution can be supposed as a liquid temperature of the cooled surface.

In the step (a), the difference between the temperature of the portion having the highest liquid temperature in the solution and the temperature of the portion having the lowest liquid temperature in the solution, immediately before generation of solidification heat, is preferably lower than or equal to 2.5° C., more preferably lower than or equal to 2.3° C., and still more preferably lower than or equal to 2.1° C. Here, the "difference in temperature immediately before the generation of solidification heat" means a difference in temperature in a case where the difference in temperature is the largest between 1 second and 10 seconds before the generation of solidification heat.

In the step (a), the temperature of the portion having the lowest liquid temperature in the solution is preferably lower than or equal to "solvent melting point −5° C", more preferably lower than or equal to "solvent melting point −5° C." and higher than or equal to "solvent melting point −20° C", and still more preferably lower than or equal to "solvent melting point −6° C." and higher than or equal to "solvent melting point −16° C". The solvent in the solvent melting point refers to a solvent of a solution of biocompatible polymers.

In the step (b), the solution of the biocompatible polymers obtained in the step (a) is frozen. The cooling temperature for the freezing in the step (b) is not particularly limited and depends on cooling equipment. However, the cooling temperature is a temperature which is lower than the temperature of the portion having the lowest liquid temperature in the solution preferably by 3° C. to 30° C., more preferably by 5° C. to 25° C., and still more preferably by 10° C. to 20° C.

In the step (c), the frozen biocompatible polymers obtained in the step (b) are freeze-dried. The freeze-drying can be performed by a usual method. For example, the freeze-drying can be performed by carrying out vacuum drying at a temperature lower than a melting point of a solvent and further carrying out vacuum drying at room temperature (20° C.).

In the present invention, a biocompatible polymer block can be produced preferably by pulverizing the porous body obtained in the above-described step (c).

(2) Cell

The types of cells used in the present invention are not particularly limited, cells having a function of treating a lysosomal storage disease, which is the purpose of the present invention, can be suitably used and any kinds of cells can be used according to an actual therapeutic purpose. In addition, one type of cells may be used, or a plurality of types of cells may be used in combination. A Cell to be used is preferably an animal cell, more preferably a vertebrate-derived cell, and particularly preferably a human-derived cell. The type of the vertebrate-derived cell (particularly, a human-derived cell) may be any of a pluripotent cell, a somatic stem cell, a precursor cell, or a mature cell and particularly preferably a somatic stem cell.

As the pluripotent cell, for example, an embryonic stem (ES) cell, a germline stem (GS) cell, or an artificial pluripotent stem (iPS) cell can be used. As the somatic stem cell, for example, a mesenchymal stem cell (MSC), a hematopoietic stem cell, an amniotic cell, a umbilical cord blood cell, a bone marrow-derived cell (for example, a bone marrow-derived MSC), a cardiac stem cell, an adipose-derived stem cell, or a neural stem cell can be used. As the precursor cell and the mature cell, for example, a cell derived from skin, dermis, epidermis, muscle, cardiac muscle, a nerve, a bone, cartilage, endothelium, a brain, epithelium, a heart, a kidney, a liver, pancreas, spleen, oral cavity, cornea, bone marrow, umbilical cord blood, amnion, or hair can be used. As the human-derived cell, for example, an ES cell, an iPS cell, a MSC, a chondrocyte, an osteoblast, an osteoprogenitor cell, a mesenchymal cell, a myoblast, a cardiac muscle cell, a cardiac myoblast, a nerve cell, a hepatocyte, a beta cell, a fibroblast, a corneal endothelial cell, a vascular endothelial cell, a corneal epithelial cell, an amniotic cell, a umbilical cord blood cell, a bone marrow-derived cell, or a hematopoietic stem cell can be used. The cell may be derived from any of an autologous cell or a heterologous cell. The cell may be a mesenchymal stem cell or an interstitial cell differentiated and induced from an ES cell or an iPS cell. Among these, it is preferable to use at least a mesenchymal stem cell or a fibroblast as the cell. An adipose-derived mesenchymal stem cell or a bone marrow-derived mesenchymal stem cell is preferable as the mesenchymal stem cell. The mesenchymal stem cell is preferably derived from a human or a dog.

The cell used in the present invention is preferably a cell which does not overexpress a gene necessary for a therapy of a lysosomal storage disease by introduction of the gene.

(3) Cell Structure

The cell structure of the present invention is a cell structure which includes a plurality of the biocompatible polymer blocks according to the present invention and a plurality of cells of at least one type and in which at least one of the polymer blocks is disposed in gaps between the plurality of cells. In the present invention, the biocompatible polymer blocks and the cells are used and the plurality of polymer blocks are three-dimensionally disposed in a mosaic pattern in the gaps between the plurality of cells. By three-dimensionally disposing the biocompatible polymer blocks and the cells in a mosaic pattern, a three-dimensional cell structure in which cells uniformly exist in the structure is formed and, as described above, material permeability is obtained.

In the cell structure of the present invention, the plurality of polymer blocks are disposed in gaps between the plurality of cells. Here, the "gaps between cells" are not necessarily spaces closed by the constituent cells, and may be interposed between the cells. Moreover, gaps are not necessarily present between all of the cells, and there may be a place where the cells are in contact with each other. The distance of a gap between cells through the polymer block, that is, the gap distance in a case of selecting a certain cell and a cell present at the shortest distance from the certain cell is not particularly limited. However, the distance is preferably the same as the size of a polymer block, and a suitable distance is also within a range of a suitable size of a polymer block.

Furthermore, the polymer blocks according to the present invention are configured to be interposed between the cells. However, cells are not necessarily present between all of the polymer blocks, and there may be a place where the polymer blocks are in contact with each other. The distance between polymer blocks through the cell, that is, the distance in a case of selecting a polymer block and a polymer block present at the shortest distance from the polymer block is not particularly limited. However, the distance is preferably the same as a size of a cluster of cells in a case where one or several cells to be used are gathered and for example, the size thereof is 10 µm to 1,000 µm, preferably 10 µm to 100 µm, and more preferably 10 µm to 50 µm.

In the present specification, the expression "uniformly exist" in "three-dimensional cell structure in which cells uniformly exist in the structure" or the like is used, but does not mean complete uniformity.

A thickness or a diameter of the cell structure of the present invention can be set to a desired thickness, but a lower limit thereof is preferably greater than or equal to 100 µm, more preferably greater than or equal to 215 µm, still more preferably greater than or equal to 400 µm, and most preferably greater than or equal to 730 µm. An upper limit of the thickness or the diameter is not particularly limited, but a general range thereof in use is preferably less than or equal to 3 cm, more preferably less than or equal to 2 cm, and still more preferably less than or equal to 1 cm. The range of the thickness or the diameter of the cell structure is preferably 100 µm to 3 cm, more preferably 400 µm to 3 cm, still more preferably 500 µm to 2 cm, and even more preferably 720 µm to 1 cm.

In the cell structure of the present invention, regions including polymer blocks and regions including cells are preferably disposed in a mosaic pattern. Moreover, in the present specification, the expression "the thickness or the diameter of the cell structure" means the followings. In a case where one point A in the cell structure is selected, a length of a line segment which divides the cell structure so that the distance from an outer boundary of the cell structure is the shortest in a straight line passing through the point A is set as a line segment A. The point A at which the line segment A becomes the longest is selected in the cell structure, and a length of the line segment A in this case is set as "a thickness or a diameter of a cell structure".

In the cell structure of the present invention, a ratio of a polymer block to a cell is not particularly limited. However, a mass of a polymer block per cell is preferably 0.0000001 µg to 1 µg, more preferably 0.000001 µg to 0.1 µg, still more preferably 0.00001 µg to 0.01 µg, and most preferably 0.00002 µg to 0.006 µg. By setting the ratio in the above range, the cells can further uniformly exist. By setting a lower limit thereof in the above range, the effect of the cell can be exhibited in case of using the cell structure for the above-described application, and by setting an upper limit thereof in the above range, components optionally present in the polymer block can be supplied to the cell. Here, the components in the polymer block are not particularly limited, but examples thereof include components contained in a medium described below.

(4) Method of Producing Cell Structure

The cell structure used in the present invention can be produced by mixing biocompatible polymer blocks and at least one type of cells. Specifically, the cell structure of the present invention can be produced by alternately disposing the biocompatible polymer blocks (cluster including biocompatible polymers) and the cells. Moreover, "alternately" does not mean complete alternation, but for example, means a state where the biocompatible polymer blocks and the cells are mixed. The production method is not particularly limited, but is preferably a method of seeding cells after a polymer block is formed. Specifically, a cell structure can be produced by incubating a mixture of the biocompatible polymer blocks and a cell-containing culture solution. For example, the cells and the biocompatible polymer blocks produced in advance are disposed in a mosaic pattern in a container or in a liquid held in a container. As a means of disposition, it is preferable to promote and control formation of mosaic-like disposition including the cells and the biocompatible polymer blocks by using spontaneous aggregation, natural falling, centrifugation, and stirring.

The container to be used is preferably a container made of a cell low-adhesive material or a cell non-adhesive material, and more preferably a container made of polystyrene, polypropylene, polyethylene, glass, polycarbonate, and polyethylene terephthalate. A shape of a bottom surface of the container is preferably a flat bottom shape, a U shape, or a V shape.

With respect to the mosaic-like cell structure obtained by the above method, a cell structure having a desired size can be produced by a method such as (a) fusing mosaic-like cell clusters which are separately prepared, or (b) increasing a volume thereof in a differentiation medium or a proliferation medium. The method of fusion and the method of increasing a volume are not particularly limited.

For example, in a step of incubating the mixture of the biocompatible polymer blocks and the cell-containing culture solution, the volume of the cell structure can be increased by replacing the medium with a differentiation medium or a proliferation medium. Preferably, in the step of incubating the mixture of the biocompatible polymer blocks and the cell-containing culture solution, a cell structure which has a desired size and in which cells uniformly exist can be produced by further adding the biocompatible polymer blocks.

Specifically, the method of fusing mosaic-like cell clusters which are separately prepared is a method of producing a cell structure including a step of fusing a plurality of cell structures which include a plurality of biocompatible polymer blocks and a plurality of cells and in which one or the plurality of biocompatible polymer blocks are disposed in a part or all of a plurality of gaps formed by the plurality of cells.

In the method of producing a cell structure used in the present invention, preferable ranges of "biocompatible polymer blocks (types, sizes, or the like)", "cells", "gaps between a plurality of cells", "obtained cell structures (sizes or the like)", "a ratio of a polymer block to a cell", and the like are the same as those described above in the present specification.

(5) Treatment Agent for Lysosomal Storage Disease

The lysosomal storage disease is a general term for diseases caused by accumulation of undecomposed substances in a lysosome, which is an intracellular organelle, due to a genetic abnormality which results in a deficiency in activity of one or a plurality of enzymes in a lysosome, or accumulation of substances in a lysosome due to dysfunction of a membrane protein in a lysosome.

The lysosomal storage diseases are classified into a plurality of types according to individually abnormal enzymes or genes, and are intractable diseases with more than 60 types.

Examples of the lysosomal storage disease include Fabry disease, Gaucher disease, sialidosis, Niemann pick type A and B, galactosialidosis, Niemann pick type C, I-cell disease, mucolipidosis type III, GM1 gangliosidosis, β-galactosidase deficiency, α-mannosidosis, GM2 gangliosidosis, β-mannosidosis, Krabbe, fucosidosis, metachromatic leukodystrophy, Aspartylglucosaminuria, Multiple sulfatase deficiency, Schindler, Farber lipogranulomatosis, Pompe disease, Hurler-Scheie syndrome, Wolman disease, Hunter syndrome, Danon disease, Sanfilippo syndrome, free sialic acid storage disease, Morquio syndrome, ceroid lipofuscinosis, Maroteaux-Lamy syndrome, Sly disease, β-glucuronidase hypoactivity disease, Sandhoff disease, and cholesterol ester storage disease. Among these, Fabry disease is preferable.

Treatment agent according to the embodiment of the present invention can reduce globotriaosylsphingosine in a living body by secreting a-galactosidase A in the living body, and thus the Fabry disease is treated.

Causative genes/proteins for the respective lysosomal storage diseases are identified in many cases. Specific examples thereof are shown in Table 1 below.

The treatment means prevention, a therapy, or the like for various diseases and the like.

The prevention means that progress of symptoms specific to a target disease is preliminarily suppressed, and includes inhibition of onset, reduction in the risk of onset, or delay of onset. The extent of suppression of progress is not limited at all, and even in a case where the extent is very small, as long as the progress can be suppressed, the suppression is included in prevention.

The therapy means improvement or suppression of progress on a state or a disease which is a target.

The treatment agent means a material provided for the purpose of the treatment.

The treatment agent for a lysosomal storage disease according to the embodiment of the present invention can be transplanted into a living body to be used. As the transplantation method, incision, injection, or an endoscope can be used. The treatment agent for a lysosomal storage disease according to the embodiment of the present invention can reduce the size of the structure unlike a cellular implant such as a cell sheet, and thus a minimally invasive transplantation method such as transplantation by injection becomes possible.

The amount of the treatment agent for a lysosomal storage disease according to the embodiment of the present invention to be transplanted can be appropriately selected according to condition of a transplant subject (human or animal) or the like, but the number of cells to be transplanted is preferably $1.0 \times 10^5$ cells/kg to $2.0 \times 10^9$ cells/kg and more preferably $1.0 \times 10^6$ cells/kg to $2.0 \times 10^8$ cells/kg.

With respect to the number of times of transplantation of the treatment agent for a lysosomal storage disease according to the embodiment of the present invention, the transplantation may be performed once or may be performed twice or more, if necessary.

(6) Various Applications

According to the present invention, there is provided a method of treating a lysosomal storage disease, including the step of transplanting the cell structure defined in the present invention to a subject in need of a treatment of a lysosomal storage disease. In the above method of treating a lysosomal storage disease, the preferable range of the cell structure is the same as described above.

According to the present invention, there is provided the cell structure defined in the present invention to be used in the treatment of the lysosomal storage disease. In the cell structure described above, the preferable range of the cell structure is the same as described above.

According to the present invention, there is provided use of the cell structure defined in the present invention for producing the treatment agent for a lysosomal storage disease. In the above use, the preferable range of the cell structure is the same as described above.

The present invention will be more specifically described using the following examples, but is not limited by the examples.

EXAMPLES

Reference Example 1

Recombinant Peptide (Recombinant Gelatin)

The following CBE3 (which is disclosed in WO2008/103041A) was prepared as a recombinant peptide (recombinant gelatin).
CBE3:
Molecular weight: 51.6 kDa
Structure: GAP[(GXY)$_{63}$]$_3$G (SEQ ID NO: 11)S
Number of amino acids: 571
Number of RGD sequences: 12
Imino acid content: 33%
Almost 100% of amino acids have a repeating structure of GXY. In the amino acid sequence of CBE3, serine, threonine, asparagine, tyrosine, and cysteine are not included. CBE3 has an ERGD sequence (SEQ ID NO: 10).
Isoelectric point: 9.34
GRAVY value: −0.682
1/IOB value: 0.323
Amino acid sequence (SEQ ID NO: 1 in a sequence listing) (which is the same as that of SEQ ID NO: 3 in WO2008/103041A. However, X at the end is corrected to "P")

GAP(GAPGLQGAPGLQGMPGERGAAGLPGPKGERGDAGPKGADGAPGAPGL

QGMPGERGAAGLPGPKGERGDAGPKGADGAPGKDGVRGLAGPIGPPGERGA

AGLPGPKGERGDAGPKGADGAPGKDGVRGLAGPIGPPGPAGAPGAPGLQGM

PGERGAAGLPGPKGERGDAGPKGADGAPGKDGVRGLAGPP)$_3$G

Reference Example 2

Production of Porous Body of Recombinant Peptide

[PTFE-Thickness-Cylindrical Container]
A cylindrical cup-shaped polytetrafluoroethylene (PTFE) container with a bottom-surface thickness of 3 mm, a diameter of 51 mm, a side-surface thickness of 8 mm, and a height of 25 mm was prepared. In a case where the cylindrical cup has a curved surface as a side surface, the side surface is closed by PTFE with 8 mm and a bottom surface (circular shape of a flat plate) is also closed by PTFE with 3 mm. In contrast, an upper surface is in an open shape. Accordingly, an inner diameter of the cylindrical cup is 43 mm. Hereinafter, this container is referred to as a PTFE-thickness-cylindrical container.

Aluminum Glass Plate-Cylindrical Container

A cylindrical cup-shaped aluminum container with a thickness of 1 mm and a diameter of 47 mm was prepared. In a case where the cylindrical cup has a curved surface as a side surface, the side surface is closed by aluminum with 1 mm and a bottom surface (circular shape of a flat plate) is also closed by aluminum with 1 mm. In contrast, an upper surface is in an open shape. In addition, TEFLON (registered trademark) with a thickness of 1 mm is evenly spread only in the inside of the side surface, and as a result, an inner diameter of the cylindrical cup is 45 mm. In addition, in the bottom surface of this container, a glass plate with 2.2 mm is bonded on the outside of aluminum. Hereinafter, this container is referred to as an aluminum glass plate-cylindrical container.

Freezing Step in which Difference in Temperature is Small, and Drying Step

A CBE3 aqueous solution was poured into the PTFE-thickness-cylindrical container or the aluminum glass plate-cylindrical container, and was cooled down from the bottom surface using a cooling shelf within a vacuum freeze dryer (TF5-85ATNNN: Takara Co., Ltd.). Combinations of setting of the container, a final concentration of the CBE3 aqueous solution, an amount of the solution, and a temperature of the shelf at this time were prepared as described below.

Condition A:

PTFE-thickness-cylindrical container, final concentration of CBE3 aqueous solution of 4 mass %, and amount of aqueous solution of 4 mL. As the setting for the temperature of the shelf, the temperature was cooled down until the temperature reached −10° C., and freezing was performed for 1 hour at −10° C., for 2 hours at −20° C., for 3 hours at −40° C., and finally for 1 hour at −50° C. Then, the frozen product was subjected to vacuum drying for 24 hours at −20° C. after the setting of the temperature of the shelf was returned to −20° C. After 24 hours, the temperature of the shelf was increased to 20° C. in a state where the vacuum drying was continued as it was, and the vacuum drying was further performed for 48 hours at 20° C. until a vacuum degree was sufficiently decreased (1.9×10$^5$ Pa). Then, the product was taken out of the vacuum freeze dryer. Therefore, a porous body was obtained.

Condition B:

Aluminum glass plate-cylindrical container, final concentration of CBE3 aqueous solution of 4 mass %, and amount of aqueous solution of 4 mL. As the setting for the temperature of the shelf, the temperature was cooled down until the temperature reached −10° C., and freezing was performed for 1 hour at −10° C., for 2 hours at −20° C., for 3 hours at −40° C., and finally for 1 hour at −50° C. Then, the frozen product was subjected to vacuum drying for 24 hours at −20° C. after the setting of the temperature of the shelf was returned to −20° C. After 24 hours, the temperature of the shelf was increased to 20° C. in a state where the vacuum drying was continued as it was, and the vacuum drying was further performed for 48 hours at 20° C. until a vacuum degree was sufficiently decreased ($1.9 \times 10^5$ Pa). Then, the product was taken out of the vacuum freeze dryer. Therefore, a porous body was obtained.

Condition C:

PTFE-thickness-cylindrical container, final concentration of CBE3 aqueous solution of 4 mass %, and amount of aqueous solution of 10 mL. As the setting for the temperature of the shelf, the temperature was cooled down until the temperature reached −10° C., and freezing was performed for 1 hour at −10° C., for 2 hours at −20° C., for 3 hours at 31 40° C., and finally for 1 hour at −50° C. Then, the frozen product was subjected to vacuum drying for 24 hours at −20° C. after the setting of the temperature of the shelf was returned to −20° C. After 24 hours, the temperature of the shelf was increased to 20° C. in a state where the vacuum drying was continued as it was, and the vacuum drying was further performed for 48 hours at 20° C. until a vacuum degree was sufficiently decreased ($1.9 \times 10^5$ Pa). Then, the product was taken out of the vacuum freeze dryer. Therefore, a porous body was obtained.

Measurement of Temperature in Each Freezing Step

Regarding each of Conditions A to C, a liquid temperature of a surface of water in a circular center portion within a container was measured as a liquid temperature (non-cooled surface liquid temperature) of the farthest portion from a cooling side in a solution, and a liquid temperature of a bottom portion within the container was measured as a liquid temperature (cooled surface liquid temperature) of the closest portion to the cooling side in the solution.

As a result, each temperature and a profile of the difference in temperature are as shown in FIGS. 1 to 3.

It can be seen from FIGS. 1 to 3 that in Conditions A to C, the liquid temperature fell below 0° C., which was a melting point, in a setting section of a temperature of a shelf of −10° C. (before the temperature was decreased to −20° C.), and the solution was in a (unfrozen and overcooled) state where freezing did not occur in that state. In addition, in this state, the difference in temperature between the cooled surface liquid temperature and the non-cooled surface liquid temperature was lower than or equal to 2.5° C. In the present specification, the "difference in temperature" means "non-cooled surface liquid temperature"–"cooled surface liquid temperature". Then, the timing at which the liquid temperature rapidly rose to around 0° C. by further decreasing the temperature of the shelf to −20° C. was confirmed, and it can be seen that freezing started due to generation of solidification heat at the timing. In addition, it was also possible to confirm that ice formation actually started at this timing. Thereafter, the temperature was around 0° C. while the certain time passed. At this time, the product was in a state where a mixture of water and ice was present. The temperature finally started to be decreased again from 0° C., and at this time, liquid disappeared and was changed to ice. Accordingly, the measured temperature was the solid temperature within the ice, that is, was not the liquid temperature.

Hereinafter, regarding Conditions A to C, the difference in temperature in a case where the non-cooled surface liquid temperature reached a melting point (0° C.), the difference in temperature immediately before the temperature of the shelf was decreased from −10° C. to −20° C., and the difference in temperature immediately before the generation of solidification heat are described. The "difference in temperature immediately before" referred to in the present invention indicates the highest temperature within the difference in temperature which can be detected between 1 second to 20 seconds before an event (such as the generation of solidification heat).

Condition A

Difference in temperature in a case where a non-cooled surface liquid temperature reached a melting point (0° C.): 1.1° C.
Difference in temperature immediately before a temperature was decreased from −10° C. to −20° C.: 0.2° C.
Difference in temperature immediately before generation of solidification heat: 1.1° C.

Condition B

Difference in temperature in a case where a non-cooled surface liquid temperature reached a melting point (0° C.): 1.0° C.
Difference in temperature immediately before a temperature was decreased from −10° C. to −20° C.: 0.1° C.
Difference in temperature immediately before generation of solidification heat: 0.9° C.

Condition C

Difference in temperature in a case where a non-cooled surface liquid temperature reached a melting point (0° C.): 1.8° C.
Difference in temperature immediately before a temperature was decreased from −10° C. to −20° C.: 1.1° C.
Difference in temperature immediately before generation of solidification heat: 2.1° C.

Reference Example 3

Production of Biocompatible Polymer Block (Pulverization and Cross-Linking of Porous Body)

The CBE3 porous bodies of Conditions A and B which were obtained in Reference Example 2 were pulverized by NEW POWER MILL (Osaka Chemical Co., Ltd., NEW POWER MILL PM-2005). The pulverization was performed by one minute×5 times, that is, for 5 minutes in total at the maximum rotation speed. The obtained pulverized substances were sized with a stainless steel sieve to obtain uncross-linked blocks with 25 to 53 μm, 53 to 106 μm, and 106 to 180 μm. Then, the uncross-linked blocks were subjected to thermal cross-linking (cross-linking was performed for times of six kinds of 8 hours, 16 hours, 24 hours, 48 hours, 72 hours, and 96 hours) at 160° C. under reduced pressure to obtained biocompatible polymer blocks (CBE3 blocks).

Hereinafter, a porous body-derived block of Condition A which is cross-linked for 48 hours is referred to as E, and a porous body-derived block of Condition B which is cross-linked for 48 hours is referred to as F. E and F are blocks with a small difference in temperature which are formed from porous bodies produced through a freezing step in which the difference in temperature is small. Moreover, since the difference in cross-linking time did not influence the performance in the evaluation of the present examples, hereafter, the blocks cross-linked for 48 hours were used as a representative. There was no difference in the performance between E and F. In reference examples, examples, and comparative examples below, biocompatible polymer blocks which satisfied Condition A, had sizes of 53 to 106 μm, and were produced with the cross-linking time of 48 hours were used.

Reference Example 4

Measurement of Tap Density of Biocompatible Polymer Block

The tap density is a value indicating how many blocks can be densely packed in a certain volume, and it can be said that as the value becomes lower, the blocks cannot be densely packed, that is, the structure of the block is complicated. The tap density was measured as follows. First, a funnel with a cap (having a cylindrical shape with a diameter of 6 mm and a length of 21.8 mm: a capacity of 0.616 cm$^3$) attached at the tip thereof was prepared, and a mass of only the cap was measured. Then, the cap was attached to the funnel, and blocks were poured from the funnel so as to be accumulated in the cap. After pouring a sufficient amount of blocks, the cap portion was hit 200 times on a hard object such as a desk, the funnel was removed, and the blocks were leveled off with a spatula. A mass was measured in a state where the cap was filled up with the blocks. The tap density was determined by calculating a mass of only the blocks from the difference between the mass of the cap filled up with the blocks and the mass of only the cap, and dividing the mass of only the blocks by the volume of the cap.

As a result, the tap density of the biocompatible polymer block of Reference Example 3 was 98 mg/cm$^3$.

Reference Example 5

Measurement of Cross-Linking Degree of Biocompatible Polymer Block

The cross-linking degree (the number of times of cross-linking per molecule) of the blocks cross-linked in Reference Example 3 was calculated. The measurement was performed by a TNBS (2,4,6-trinitrobenzene sulfonic acid) method.

Sample Preparation

A sample (about 10 mg), 4 mass % NaHCO$_3$ aqueous solution (1 mL), and 1 mass % TNBS aqueous solution (2 mL) were added to a glass vial, and the mixture was shaken for 3 hours at 37° C. Thereafter, 37 mass % hydrochloric acid (10 mL) and pure water (5 mL) were added thereto, and then the mixture was allowed to stand for 16 hours or longer at 37° C. to prepare a sample.

Preparation of Blank

A sample (about 10 mg), 4 mass % NaHCO$_3$ aqueous solution (1 mL), and 1 mass % TNBS aqueous solution (2 mL) were added to a glass vial, 37 mass % hydrochloric acid (3 mL) was immediately added thereto, and the mixture was shaken for 3 hours at 37° C. Thereafter, 37 mass % hydrochloric acid (7 mL) and pure water (5 mL) were added thereto, and then the mixture was allowed to stand for 16 hours or longer at 37° C. to prepare a blank.

The absorbances (345 nm) of the sample and the blank which were diluted 10 times with pure water were measured, and the cross-linking degree (the number of times of cross-linking per molecule) was calculated from (Expression 2) and (Expression 3).

$$(As-Ab)/14{,}600 \times V/w \qquad \text{(Expression 2)}$$

(Expression 2) represents the amount (molar equivalent) of lysine per 1 g of a recombinant peptide.

(In the expression, As represents a sample absorbance, Ab represents a blank absorbance, V represents an amount (g) of reaction liquid, and w represents a mass (mg) of the recombinant peptide.)

$$1 \times (\text{sample (Expression 2)/uncross-linked recombinant peptide (Expression 2)}) \times 34 \qquad \text{(Expression 3)}$$

(Expression 3) represents the number of times of cross-linking per molecule.

As a result, the cross-linking degree of the biocompatible polymer blocks of Reference Example 3 was 4.2.

Reference Example 6

Measurement of Water Absorption Rate of Biocompatible Polymer Block

The water absorption rate of biocompatible polymer block produced in Reference Example 3 was calculated.

A 3 cm×3 cm bag made of nylon mesh was filled with about 15 mg of the biocompatible polymer block at 25° C., was swollen in ion exchange water for 2 hours, and then was dried with air for 10 minutes. The mass of the bag was measured at each stage, and the water absorption rate was determined according to (Expression 4).

$$\text{Water absorption rate} = (w2 - w1 - w0)/w0 \qquad \text{(Expression 4)}$$

(In the expression, w0 represents a mass of a material before water absorption, w1 represents a mass of an empty bag after water absorption, and w2 represents a mass of the whole bag containing the material after water absorption.)

As a result, the water absorption rate of the block of Reference Example 3 was 786%.

Reference Example 7

Test for Confirming Expression of Lysosomal Storage Disease-Related Enzyme in Cell Regarding a human bone marrow-derived mesenchymal stem cell (hBMSC), a human adipose-derived stem cell (hADSC), a human dental pulp-derived stem cell (hDPSC), the presence or absence of expression of lysosomal storage disease-related enzymes was evaluated by detecting mRNAs in the cells with a polymerase chain reaction (PCR). As a result, as shown in FIGS. 4 to 7, it was found that the hBMSC, the hADSC, and the hDPSC expressed genes of 50 types of related enzymes shown in the following table. In FIGS. 4 to 7, the hBMSC, the hADSC, and the hDPSC are denoted as BMSC, ADSC, and DPSC, respectively, and P5 represents a fifth passage.

TABLE 1

| | Causative gene/protein | Abbreviation | Disease name |
|---|---|---|---|
| 1 | α-Sialidase | NEU1 | Sialidosis |
| 2 | Cathepsin A | CTSA (PPCA) | Galactosialidosis |
| 3 | α-Mannosidase | MAN2B1 | α-Mannosidosis |
| 4 | β-Mannosidase | MANBA | β-Mannosidosis |
| 5 | Glycosylasparaginase | AGA | Aspartylglucosaminuria |
| 6 | α-Fucosidase | FUCA1 | Fucosidosis |
| 7 | α-N-Acetylglucosaminidase | NAGA | Schindler |
| 8 | β-Galactosidase | GLB1 | GM1 gangliosidosis/MPS IVB |
| 9 | β-Hexosaminidase α-subunit | HEXA | GM2-gangliosidosis (Tay-Sachs) |
| 10 | β-Hexosaminidase β-subunit | HEXB | GM2-gangliosidosis (Sandhoff) |
| 11 | GM2 activator protein | GM2A | GM2 gangliosidosis |
| 12 | Glucocerebrosidase | GBA | Gaucher disease |
| 13 | Saposin C (or prosaposin) | PSAP | |
| 14 | Arylsulfatase A | ARSA | Metachromatic leukodystrophy (MLD) |
| 15 | Saposin B (or prosaposin) | PSAP | |
| 16 | Formyl-Glycin generating enzyme | SUMF1 | Multiple sulfatase deficiency |
| 17 | β-Galactosylceramidase | GALC | Globoid cell leukodystrophy (Krabbe) |
| 18 | α-Galactosidase A (αGalA) | GLA | Fabry |
| 19 | Iduronate 2-sulfatase | IDS | MPS II (Hunter) |
| 20 | α-Iduronidase | IDUA | MPS I (Hurler, Scheie) |
| 21 | Heparan N-sulfatase | SGSH | MPS IIIa (Sanfilippo A) |
| 22 | N-acetyl glucosaminidase | NAGLU | MPS IIIb (Sanfilippo B) |
| 23 | Acetyl-CoA transferase | HGSNAT | MPS IIIc (Sanfilippo C) |
| 24 | N-acetyl glucosamine 6-sulfatase | GNS | MPS IIId (Sanfilippo D) |
| 25 | β-glucuronidase | GUSB | MPS VII (Sly) |
| 26 | Arylsulfatase B | ARSB | MPS VI (Maroteaux-Lamy) |
| 27 | Galactose 6-sulfatase | GALNS | MPS IVA (Morquio A) |
| 28 | Hyaluronidase1 | HYAL1 | MPS IX |
| 29 | α-Glucosidase | GAA | Pompe |
| 30 | Acid sphingomyelinase | SMPD1 | Niemann Pick type A and B |
| 31 | Acid ceramidase | ASAH1 | Farber lipogranulomatosis |
| 32 | Acid lipase | LIPA | Wolman and cholesteryl ester storage disease |
| 33 | Cathepsin K | CTSK | Pycnodystostosis |
| 34 | Tripeptidyl peptidase (TPP1) | CLN2 (TPP1) | Ceroide lipofuscinosis 2 |
| 35 | Palmitoyl-protein thioesterase (PPT1) | CLN1 (PPT1) | Ceroide lipofuscinosis 1 |
| 36 | UDP-GlcNac phosphotransferase, α/β subunits | GNPTAB | Mucolipidosis II/Mucolipidosis IIIA |
| 37 | UDP-GlcNac phosphotransferase, γ subunits | GNPTG | Mucolipidosis IIIB |
| 38 | Cystinosin (cystin transport) | CTNS | Cystinosis |
| 39 | Sialin (sialic acid transport) | SLC17A5 | Salla disease |
| 40 | Mucolipin-1 (cation channel) | MCOLN1 | Mucolipidosis IV |
| 41 | LAMP-2 | LAMP2 | Danon |
| 42 | NPC1 | NPC1 | Niemann Pick type C |
| 43 | CLN3 | CLN3 | Ceroid lipofuscinosis 3 |
| 44 | CLN6 | CLN6 | Ceroid lipofuscinosis 6 |
| 45 | CLN8 | CLN8 | Ceroid lipofuscinosis 8 |
| 46 | LYST | LYST | Chediak-Higashi |
| 47 | MYO5A | MYO5A | Griscelli Type 1 |
| 48 | RAB27A | RAB27A | Griscelli Type 2 |
| 49 | Melanophilin | MLPH | Griscelli Type 3 |
| 50 | AP3 β-subunit | AP3B1 | Hermansky Pudliak 2 |

Example 1

Secretion Test of Lysosomal Storage Disease-Related Enzyme from Cell Structure (Mosaic Cell Cluster)

Preparation of Cell Structure

A human bone marrow-derived mesenchymal stem cell (hBMSC) was adjusted to 100,000 cells/mL in a medium including a Dulbecco's modified eagle medium (D-MEM) and 10% fetal bovine serum (FBS), the biocompatible polymer blocks (53 to 106 μm) produced in Reference Example 3 were added thereto so as to be 0.1 mg/mL, and then 200 μL thereof was seeded on a Sumilon Celltight X96U plate (Sumitomo Bakelite Co., Ltd., a bottom has a U shape). A resultant was centrifuged (600 g, 5 minutes) with a tabletop plate centrifuge and was allowed to stand for 24 hours to produce a spherical mosaic cell cluster which had a diameter of 1 mm and included the biocompatible polymer blocks and the hBMSC cells (block of 0.001 μg per cell). Since the mosaic cell cluster was produced in a U-shaped plate, this mosaic cell cluster was spherical.

Figure 8:
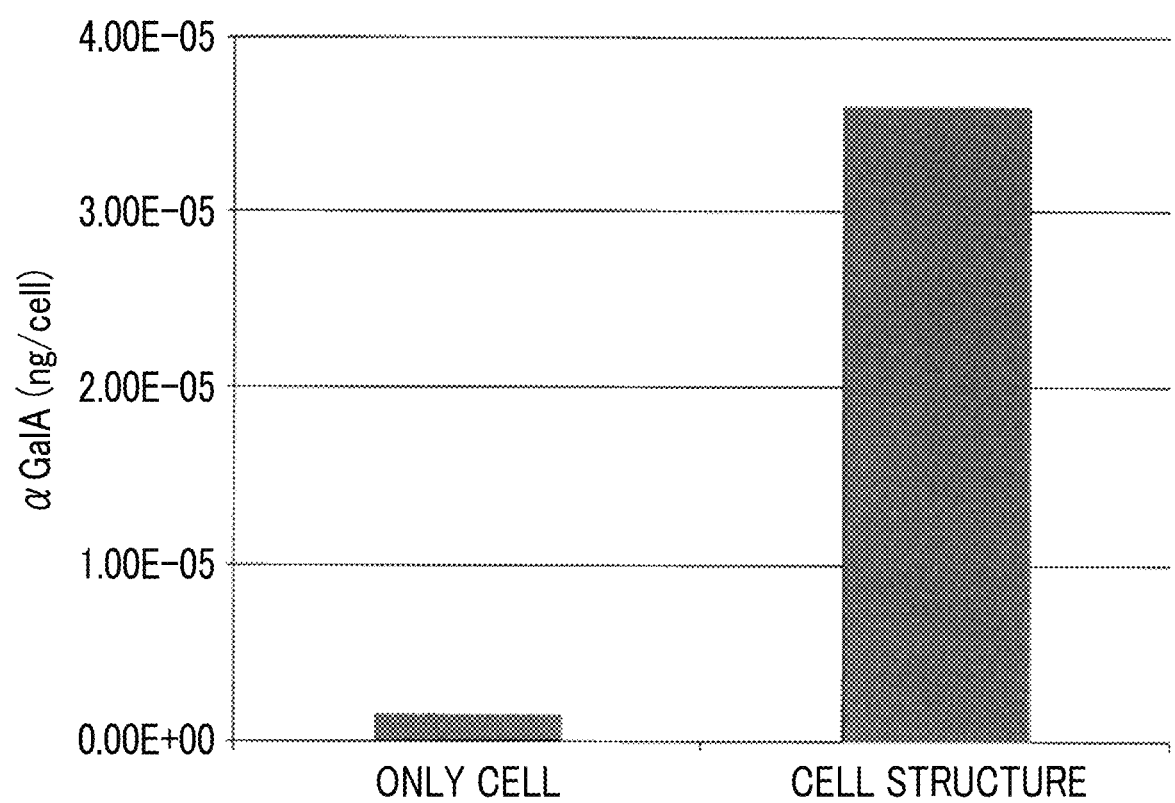
FIG. 8 illustrates results obtained by measuring an amount of an α Gal A enzyme secreted from a cell or a cell structure.

Measurement of Secretion Amount of Lysosomal Storage Disease-Related Enzyme:

Regarding the cell structure obtained as described above, an α Gal A which was contained in a supernatant after culturing for 48 hours and was a causative enzyme of a lysosomal storage disease was measured by an enzyme-linked immunosorbent assay (ELISA) (GLA/ALPHA Galactosidase ELISA Kit, LifeSpan Biosciences, LS-F-10765-1). Moreover, for comparison, the measurement was also performed on a supernatant obtained in a case where plate culture was performed with the same number of cells without forming the cell structure. As a result, as shown in FIG. 8, it was found that the secretion amount of the α Gal A (another name: GLA) enzyme per one cell was $1.5 \times 10^{-6}$ ng/cell in plate culturing (only cells) but is $3.6 \times 10^{-5}$ ng/cell in the cell structure, and unexpectedly, the secretion amount of the α Gal A enzyme from the cell structure was dramatically (about 24 times) increased.

Example 2

Production of Cell Structure (Mosaic Cell Cluster)

Mouse adipose-derived stem cells (mADSCs) were suspended in a D-MEM medium containing 10% FBS, the biocompatible polymer blocks (53 to 106 μm) produced in Reference Example 3 was added thereto, and finally, the mADSCs ($1.2 \times 10^8$ cells) and the biocompatible polymer blocks (0.25 mg) were seeded in EZSPHERE (registered trademark) dish Type 903 which is a cell non-adhesive dish of 35 mm (a spheroid well diameter is 800 μm, a spheroid well depth is 300 μm, the number of spheroid wells is about 1,200, a bottom surface is a culture surface having recessed portions, and a side outer wall portion standing on the periphery of the culture surface is provided. manufactured by AGC TECHNO GLASS CO., Ltd.) in a state of being suspended in a medium of 4 mL. The resultant was allowed to stand for 48 hours at 37° C. in a $CO_2$ incubator to obtain about 1,200 uniform cell structures.

Example 3

Effectiveness Test in Mouse with Fabry Disease

As a mouse with Fabry disease, a 6-week mouse of B6;129-Glawblo/GrsrJ (Charles River Laboratories International, Inc.) was used. In the mouse, it is known that LysoGb3 is accumulated as a disease-causing substance in a liver, and this is a cause of Fabry disease. In the effectiveness test, evaluation was performed by administering a test substance and measuring whether the amount of the LysoGb3 in the liver was decreased after four weeks. Moreover, the LysoGb3 was quantified by liquid chromatography-mass spectrometry/mass spectrometry (LC-MS/MS) and evaluated by normalization with the total mass of the protein. Specifically, evaluation was performed as follows.

The cell structure of the mADSC produced in Example 2 was administered via a portal vein, by subcutaneous administration, or by administration into a caudal vein. Regarding a dosage, the mADSC was administered as a cell structure so that the number of the cell structures was 400 ($4.0 \times 10^5$ cells of the cell+0.08 mg of the polymer block) per mouse. By quantifying the amount of the LysoGb3 in the liver four weeks after administration by the LC-MS/MS, it was evaluated whether the amount of LysoGb3 was reduced as compared with a mouse with Fabry disease to which the cell structure was not administered.

Measurement conditions of the LC-MS/MS are shown below.

Reagent

As an internal standard substance, N,N-dimethyl-D-erythro-sphingosine was used. Lyso-Gb3 and N,N-dimethyl-D-erythro-sphingosine were purchased from Matreya, LLC (Pleasant Gap, PA). Methanol (MeOH, LC-MS grade) used for the sample preparation and the LC-MS/MS and formic acid (FA, LC-MS grade) were purchased from Wako Pure Chemical Corporation.

Pierce BCA Protein Assay Kit (Thermo Fisher Scientific Inc., Waltham, MA, USA) was used for the protein quantification.

Sample Preparation

Mouse organs were collected from a healthy mouse, a mouse with Fabry disease to which the cell structure of the mADSC was administered, and a mouse with Fabry disease to which the cell structure of the mADSC was not administered, and were quickly frozen in liquid nitrogen. The frozen organs were pulverized using MULTI-BEADS SHOCKER (Yasui Kikai Corporation), and phosphate buffered saline (PBS) was added thereto in an amount of 10 times more than a tissue weight to obtain organ suspensions. First, N,N-dimethyl-D-erythro-sphingosine was diluted with methanol so that a final concentration thereof was 0.5 ng/mL to produce an internal standard solution (IS solution). Subsequently, a standard sample was produced. Specifically, 100 μL of a methanol solution of the internal standard substance was added to 20 μL of the organ suspension of the healthy mouse, and 5 μL of the Lyso-Gb3 solution was added thereto so that the final concentrations were 0, 2, 4, 20, 40, and 200 nmol/L to produce standard samples. The resultants were mixed and then centrifuged to remove a protein. On the other hand, even in a case of organs of the mouse with Fabry disease to which the cell structure of the mADSC was administered and the mouse with Fabry disease to which the cell structure of the mADSC was not administered, each organ suspension was similarly produced, 100 μL of the methanol solution of the internal standard substance was added to 20 μl of the organ suspension, 5 μL of methanol was added thereto, and the resultants were mixed and then centrifuged to remove a protein. After centrifugation, 80 μL of a 0.1% formic acid aqueous solution was added to and mixed with 80 μL of a supernatant of the obtained liquid mixture. The liquid mixture was centrifuged, then a supernatant thereof was diluted 4-fold with the 0.1% formic acid aqueous solution/50% methanol, and the obtained sample was injected to an ultra performance liquid chromatography (UPLC)-MS/MS system.

Equipment and Quantification Method

In the UPLC system, ACQUITY UPLC (Waters, Milford, MA, USA) was used as LC. A sample injection amount was 5 μL, and as a column, ACQUITY UPLC BEH Phenyl Column, 130 angstroms (A), 1.7 μm, 2.1 mm×50 mm (Waters) was used. A 0.1% formic acid aqueous solution was used as a solvent A, a 0.1% formic acid-methanol solution was used as a solvent B, and a gradient for 4.5 minutes was used (0 minutes, 50% solvent B; 0.5 minutes, 70% solvent B; 1 minute, 90% solvent B; 2.5 minutes, 100% solvent B; 3.5 minutes, 100% solvent B; 3.51 minutes, 50% solvent B; 4.5 minutes, 50% solvent B). The flow rate was 0.4 μL/min. Triple Quad5500 (AB SCIEX Framingham, MA, US) was used as MS. The quantification of Lyso-Gb3 was performed in a multiple reaction monitoring (MRM) mode. A mass as a target was set to m/z 786.336 for Lyso-Gb3 and m/z 328.190 for Lyso-Gb3-IS. For quantification, the strongest peak derived from sphingosine was used. m/z 282.400 was set for Lyso-Gb3 and m/z 110.000 was set for Lyso-Gb3-IS.

Protein Quantification Method

In the protein quantification, BSA for a calibration curve was produced by using 2 mg/mL of Albumin Standard Ampules attached to a kit and performing dilution with a solvent having the same composition as that of the sample injected to the LC-MS/MS so that the final concentrations were 2000, 1500, 1000, 750, 500, 250, 125, 25, and 0 µg/mL. For detection, TECAN infinite F200 was used and an absorbance at 550 nm was measured.

Based on the result of the analysis by the LC-MS/MS system and the result of the protein quantification by the BCA Assay, in each organ of the healthy mouse, the mouse with Fabry disease to which the cell structure of the mADSC was administered, and the mouse with Fabry disease to which the cell structure of the mADSC was not administered, the concentration of Lyso-Gb3 was calculated. That is, the amount of the Lyso-Gb3 by the LC-MS/MS was expressed by x (nmol/mL), the protein mass by the BCA Assay was expressed by y (mg/mL), and the amount of the Lyso-Gb3 was expressed by x/y (nmol/mg protein).

Figure 9:
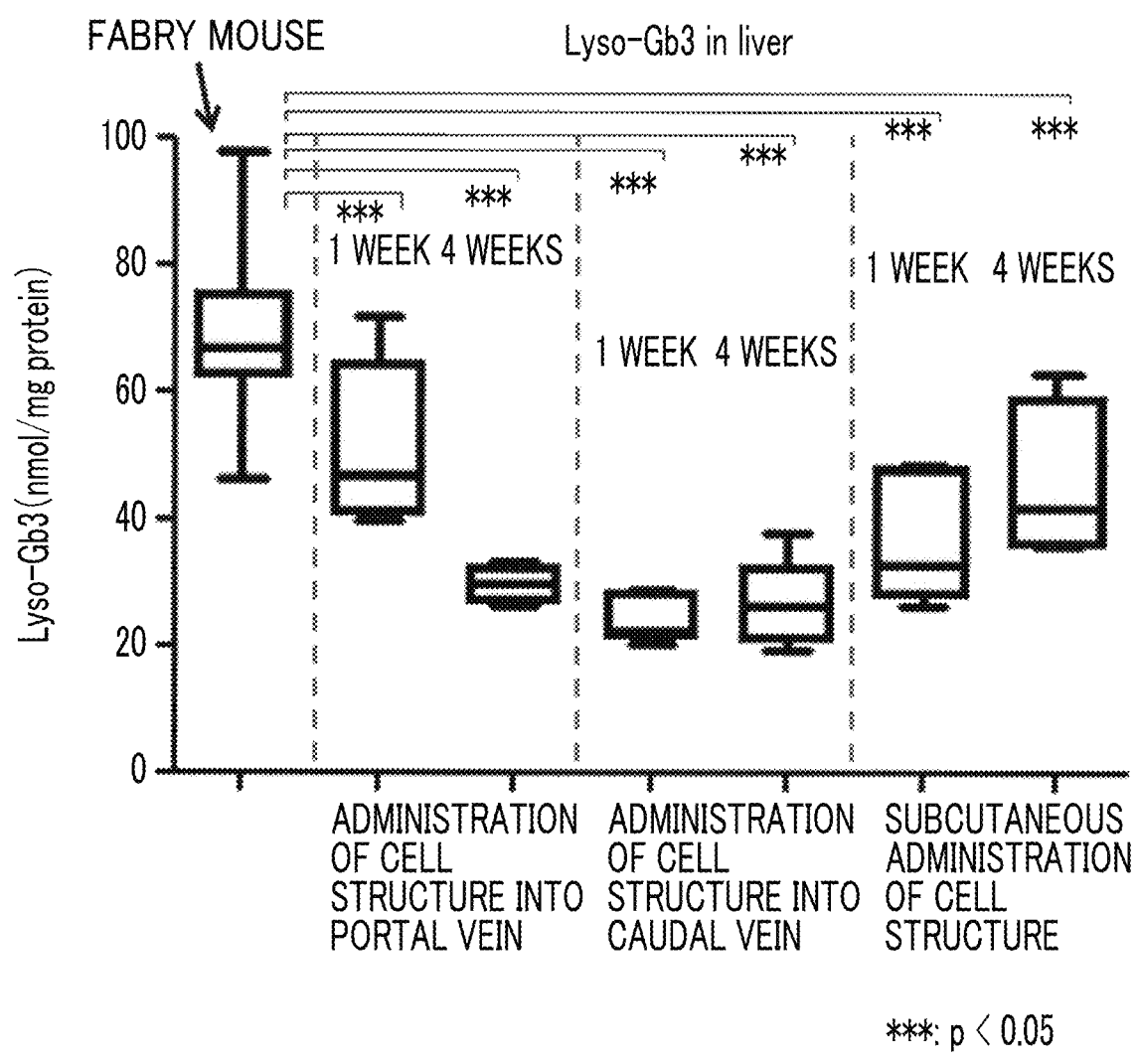
FIG. 9 illustrates results obtained by quantifying an amount of globotriaosylsphingosine (LysoGb3) in a liver four weeks after the cell structure is administered from various administration routes.

As a result, as shown in Table 2 and FIG. 9, it was found that in a group in which the cell structure was administered into a portal vein, the amount of the LysoGb3 in the liver one week after administration was significantly reduced (52 nmol/mg protein), compared with an individual (69 nmol/mg protein) to which the cell structure was not administered, and the amount of the LysoGb3 in the liver four weeks after administration was further significantly reduced (30 nmol/mg protein).

In the present specification, a Fabry mouse means a mouse with Fabry disease.

TABLE 21

| Lyso-Gb3 (nmol/mg protein) | | | | | | |
|---|---|---|---|---|---|---|
| Fabry mouse (non-administration group) (n = 10) | Administration of cell structure into portal vein | | Administration of cell structure into caudal vein | | Subcutaneous administration of cell structure | |
| | 1 week (n = 6) | 4 weeks (n = 6) | 1 week (n = 7) | 4 weeks (n = 6) | 1 week (n = 7) | 4 weeks (n = 7) |
| 46.1 | 39.7 | 33.3 | 23.0 | 21.1 | 26.1 | 41.6 |
| 70.8 | 41.2 | 26.4 | 20.3 | 19.2 | 28.0 | 41.4 |
| 68.9 | 42.5 | 31.8 | 22.4 | 24.7 | 29.2 | 35.8 |
| 57.6 | 71.7 | 31.7 | 21.4 | 27.9 | 32.8 | 35.6 |
| 63.9 | 61.8 | 28.3 | 22.0 | 37.8 | 40.8 | 58.7 |
| 97.9 | 51.6 | 27.1 | 29.0 | 30.7 | 47.8 | 54.6 |
| 64.1 | | | 28.4 | | 48.3 | 62.9 |
| 75.0 | | | | | | |
| 75.9 | | | | | | |
| 65.0 | | | | | | |

Furthermore, it was found that even in a case of an individual subjected to administration into a caudal vein, significant reduction (24 nmol/mg protein) was exhibited at one week after administration and significant reduction (27 nmol/mg protein) was exhibited even at four weeks after administration. Even in a case of subcutaneous administration, the results were similar.

Figure 10:
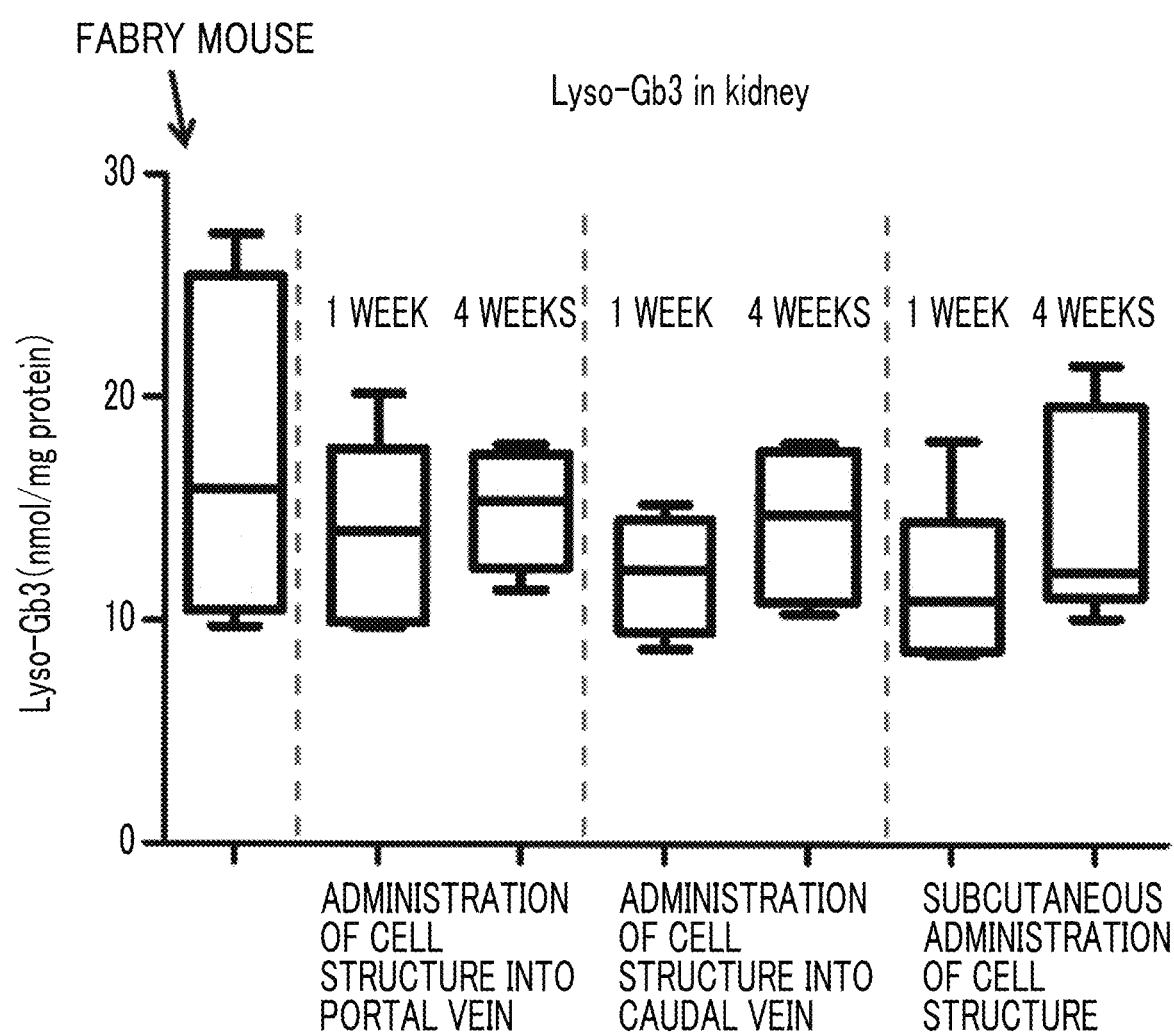
FIG. 10 illustrates results obtained by quantifying an amount of LysoGb3 in a kidney four weeks after the cell structure is administered from various administration routes.
Figure 11:
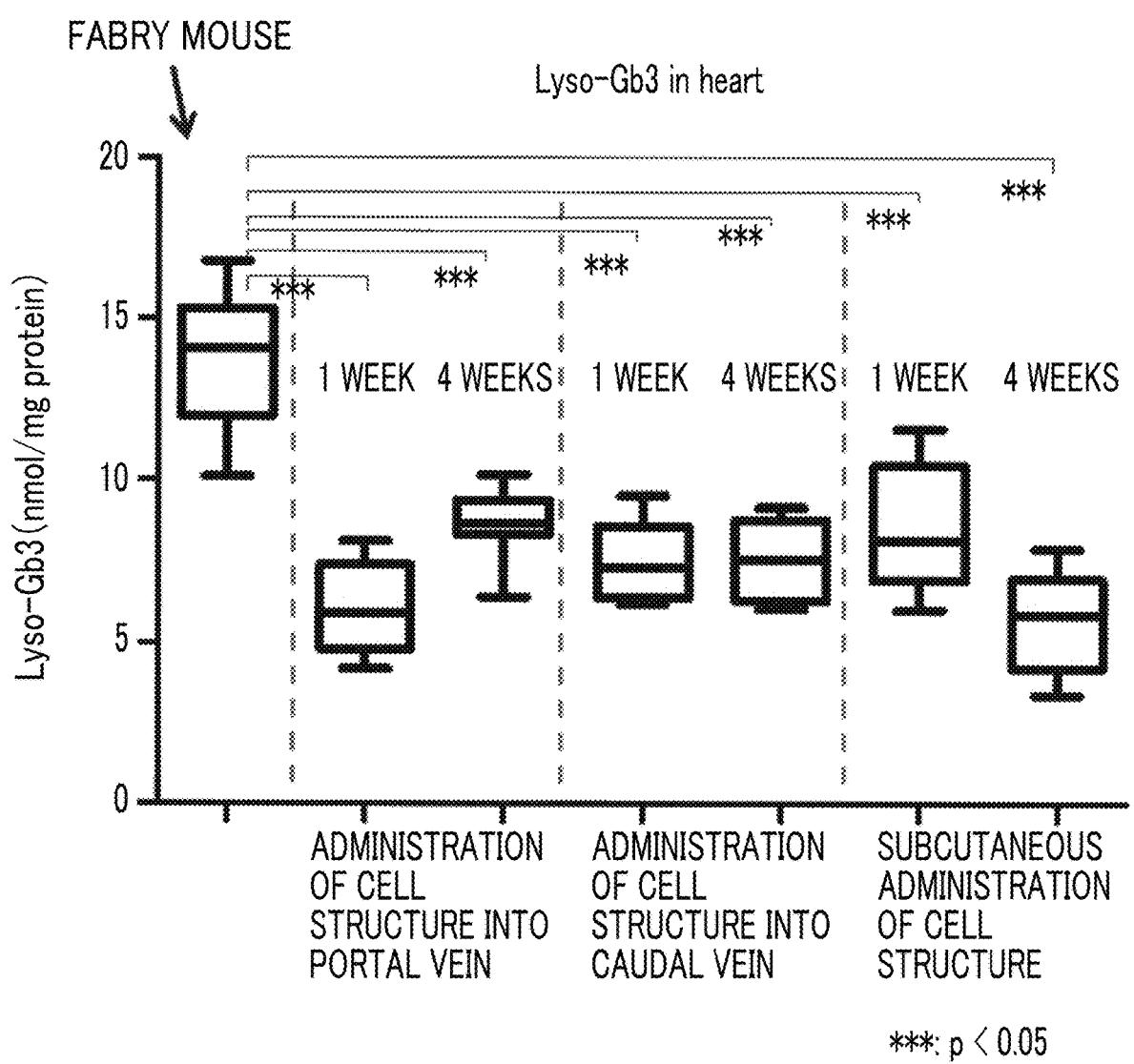
FIG. 11 illustrates results obtained by quantifying an amount of LysoGb3 in a heart four weeks after the cell structure is administered from various administration routes.

Table 3 and FIG. 10 show the amount of Lyso-Gb3 in a kidney and Table 4 and FIG. 11 show the amount of Lyso-Gb3 in a heart. Regarding the amount of the Lyso-Gb3 in the heart shown in Table 4 and FIG. 11, it was found that similar to the liver, in the group in which the cell structure was administered, the amount of the Lyso-Gb3 was significantly reduced, compared with the group in which the cell structure was not administered.

TABLE 3

| Lyso-Gb3 (nmol/mg protein) | | | | | | |
|---|---|---|---|---|---|---|
| Fabry mouse (non-administration group) (n = 10) | Administration of cell structure into portal vein | | Administration of cell structure into caudal vein | | Subcutaneous administration of cell structure | |
| | 1 week (n = 6) | 4 weeks (n = 8) | 1 week (n = 7) | 4 weeks (n = 6) | 1 week (n = 7) | 4 weeks (n = 7) |
| 10.5 | 9.7 | 11.4 | 9.8 | 11.0 | 8.9 | 10.1 |
| 10.5 | 10.0 | 12.2 | 8.7 | 10.3 | 8.6 | 11.7 |
| 11.0 | 12.3 | 17.6 | 9.5 | 12.5 | 10.9 | 11.1 |
| 11.4 | 20.2 | 17.9 | 12.3 | 17.1 | 8.5 | 12.2 |
| 9.8 | 16.8 | 12.8 | 14.4 | 17.9 | 14.2 | 21.5 |
| 25.4 | 15.7 | 13.9 | 14.6 | 17.5 | 18.1 | 19.6 |
| 23.8 | | 16.9 | 15.2 | | 14.5 | 18.0 |
| 27.3 | | 17.1 | | | | |
| 20.4 | | | | | | |
| 25.6 | | | | | | |

TABLE 4

| Lyso-Gb3 (nmol/mg protein) | | | | | | |
|---|---|---|---|---|---|---|
| Fabry mouse (non-administration group) (n = 9) | Administration of cell structure into portal vein | | Administration of cell structure into caudal vein | | Subcutaneous administration of cell structure | |
| | 1 week (n = 6) | 4 weeks (n = 8) | 1 week (n = 7) | 4 weeks (n = 6) | 1 week (n = 7) | 4 weeks (n = 7) |
| 13.8 | 4.2 | 8.7 | 6.2 | 7.2 | 6.9 | 6.5 |
| 12.7 | 5.3 | 9.1 | 6.4 | 7.9 | 8.5 | 5.9 |
| 10.1 | 5.0 | 10.2 | 7.1 | 6.4 | 7.7 | 3.4 |
| 11.3 | 8.2 | 8.7 | 7.4 | 8.7 | 6.0 | 4.9 |
| 15.8 | 7.2 | 6.4 | 8.6 | 6.0 | 8.2 | 7.0 |
| 14.9 | 6.5 | 8.3 | 8.5 | 9.2 | 10.5 | 4.2 |
| 14.1 | | 8.6 | 9.5 | | 11.6 | 7.9 |
| 16.8 | | 9.5 | | | | |
| 14.1 | | | | | | |

Figure 12:
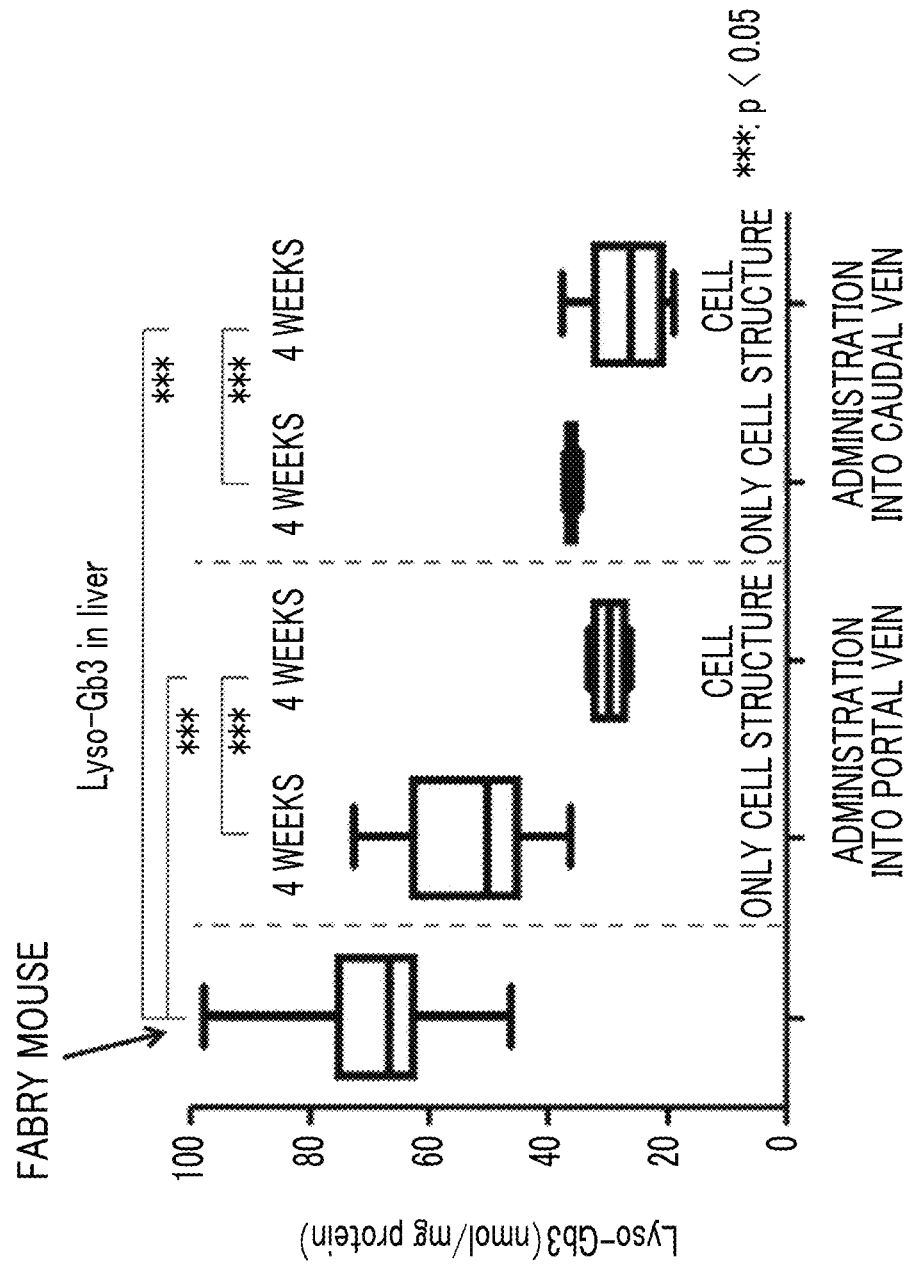
FIG. 12 illustrates results obtained by quantifying an amount of LysoGb3 in a liver four weeks after the cell or the cell structure is administered into a portal vein or a caudal vein.

Furthermore, it was also confirmed that in a case where only the mADSU was administered into a portal vein or a caudal vein with the same number of cells (4.0×10⁵ cells/mouse) for comparison, reduction in the amount of the LysoGb3 (administration into a portal vein: 30 nmol/mg protein, administration into a caudal vein: 27 nmol/mg protein) in the liver four weeks after the cell structure was administered was significantly larger, compared with the amount of the LysoGb3 (administration into a portal vein: 53 nmol/mg protein, administration into a caudal vein: 36 nmol/mg protein) in the liver four weeks after administration. The results are shown in FIG. 12.

TABLE 5

| Lyso-Gb3 (nmol/mg protein) | | | | |
|---|---|---|---|---|
| Fabry mouse (non-administration group) (n = 10) | Administration of only cell into portal vein (4 weeks) (n = 6) | Administration of cell structure into portal vein (4 weeks) (n = 6) | Administration of only cell into caudal vein (4 weeks) (n = 5) | Administration of cell structure into caudal vein (4 weeks) (n = 6) |
| 46.1 | 36.5 | 33.3 | 36.8 | 21.1 |
| 70.8 | 72.8 | 26.4 | 35.8 | 19.2 |
| 68.9 | 49.6 | 31.8 | 37.3 | 24.7 |
| 57.6 | 47.7 | 31.7 | 34.7 | 27.9 |

TABLE 5-continued

| | Lyso-Gb3 (nmol/mg protein) | | | |
|---|---|---|---|---|
| Fabry mouse (non-administration group) (n = 10) | Administration of only cell into portal vein (4 weeks) (n = 6) | Administration of cell structure into portal vein (4 weeks) (n = 6) | Administration of only cell into caudal vein (4 weeks) (n = 5) | Administration of cell structure into caudal vein (4 weeks) (n = 6) |
| 63.9 | 50.8 | 28.3 | 36.2 | 37.8 |
| 97.9 | 59.3 | 27.1 | | 30.7 |
| 64.1 | | | | |
| 75.0 | | | | |
| 75.9 | | | | |
| 65.0 | | | | |

From the results, it was clarified that in a case where a cell was administered as a cell structure, unexpectedly, high effectiveness for a mouse with Fabry disease was exhibited.

Example 4

Production of Cell Structure (Mosaic Cell Cluster)

Mouse embryonic fibroblasts (MEF) were suspended in a D-MEM medium containing 10% FBS and adjusted to 100,000 cells/mL, the biocompatible polymer blocks (53 to 106 μm) produced in Reference Example 3 were added thereto so as to be 0.1 mg/mL, and then 200 μL thereof was seeded on a Sumilon Celltight X96U plate (Sumitomo Bakelite Co., Ltd., a bottom has a U shape). A resultant was centrifuged (600 g, 5 minutes) with a tabletop plate centrifuge and was allowed to stand for 24 hours to produce a spherical mosaic cell cluster which had a diameter of 1 mm and included the biocompatible polymer blocks and the MEF cells (block of 0.001 μg per cell). Since the cell structure was produced in a U-shaped plate, this cell structure was spherical.

Thereafter, the entire content of 100 wells was transferred to 30-mL SINGLE-USE BIOREACTOR (trade name, ABLE Corporation, BWV-S03A) (a second culture vessel comprising a stirring means) with a pipette, and was stirred and cultured for seven days in a medium of 30 mL to obtain a cell structure. As a result, the number of the cell structures was 100.

Example 5

Effectiveness Test in Mouse with Fabry Disease

Figure 13:
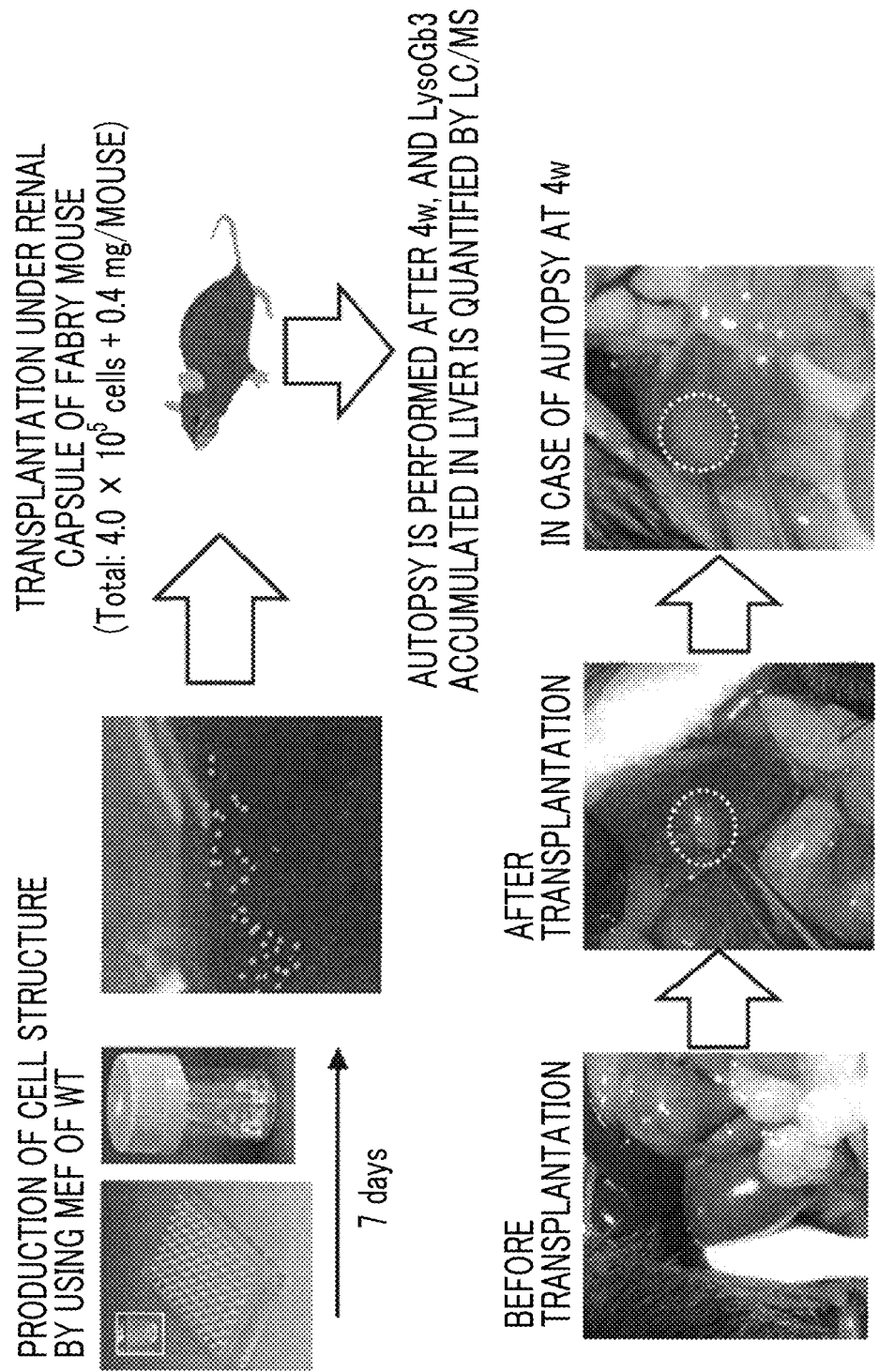
FIG. 13 illustrates a flow of a test for quantifying an amount of LysoGb3 in a liver four weeks after the cell structure is transplanted under renal capsule.

In the same manner as in Example 3, whether the amount of the LysoGb3 in the liver was decreased by administration into a mouse with Fabry disease was evaluated. 20 or 40 cell structures of the MEF produced in Example 4 were transplanted under the renal capsule. In addition, in a case where 20 cell structures were transplanted, the number of cells per mouse was $4.0 \times 10^5$ cells and 0.4 mg of the polymer block was administered, and in a case where 40 cell structures were transplanted, the number of cells per mouse was $8.0 \times 10^5$ cells and 0.8 mg of the polymer block was administered. The flow of the test is shown in FIG. 13.

As a result, as shown in Table 6 and FIG. 14, in a group in which the cell structure was transplanted under the renal capsule (the 20 cell structures-transplanted group and the 40 cell structures-transplanted group), the amount of the LysoGb3 in the liver four weeks after administration was significantly reduced, compared with an individual (56 nmol/mg protein) to which the cell structure was not administered. Moreover, reduction was further strongly observed in the 40 cell structures-transplanted group (39 nmol/mg protein) than in the 20 cell structures-transplanted group (43 nmol/mg protein).

TABLE 6

| | Lyso-Gb3 (nmol/mg protein) | |
|---|---|---|
| Non-administration group of Fabry mouse (n = 11) | Transplantation of 20 cell structures (n = 7) | Transplantation of 40 cell structures (n = 3) |
| 59.0 | 41.5 | 39.7 |
| 62.0 | 41.2 | 39.8 |
| 62.7 | 41.5 | 37.6 |
| 59.2 | 50.4 | |
| 50.3 | 49.0 | |
| 57.7 | 43.2 | |
| 59.6 | 37.0 | |
| 46.1 | | |
| 56.5 | | |
| 47.5 | | |
| 52.1 | | |

Figure 15:
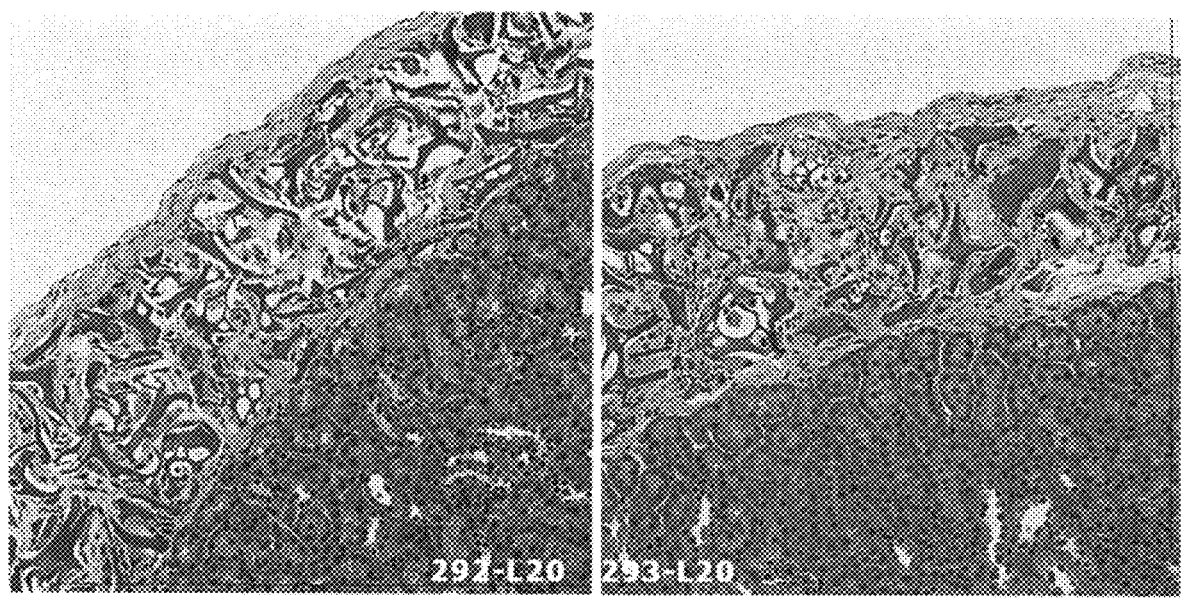
FIG. 15 illustrates a hematoxylin and eosin (HE) stained image of the cell structure under the renal capsule four weeks after the cell structure is transplanted under the renal capsule.

Furthermore, a tissue section in a transplant site four weeks after transplantation was produced and histological evaluation was performed thereon. As a result, as shown in FIG. 15, the cells and the polymer blocks were observed even four weeks after transplantation and blood vessels induced in the cell structure were also observed. Nutrient or oxygen is supplied from the blood vessel to the cell in the cell structure, and thus the effect caused by this phenomenon is expected to continue even afterwards.

Sequence Listing

International Application 17F01407W1JP18024879_8. app Based on the International Patent Cooperation Treaty

What is claimed is:

1. A method of treating a lysosomal storage disease, comprising transplanting a cell structure to a subject in need of a treatment for a lysosomal storage disease, wherein the cell structure includes a plurality of biocompatible polymer blocks and a plurality of mesenchymal stem cells, further wherein at least one of the polymer blocks is disposed in gaps between the plurality of mesenchymal stem cells,
wherein the cells do not overexpress a gene necessary for a therapy of a lysosomal storage disease by introduction of the gene,
wherein the number of mesenchymal stem cells transplanted by the cell structure is $1.0 \times 10^5$ cells/kg to $2.0 \times 10^8$ cells/kg, and
wherein the number of cells to be administered to the subject is $1.0 \times 10^5$ cells/kg to $2.0 \times 10^8$ cells/kg,
provided that the lysosomal storage disease is not metachromatic leukodystrophy, Hurler syndrome, or Hunter syndrome.

2. The method according to claim 1,
wherein the cells include at least a mesenchymal stem cell derived from a human or a dog.

3. The method according to claim 1,
wherein the cell structure includes 0.0000001 µg to 1 µg of the biocompatible polymer block per cell.

4. The method according to claim 1,
wherein a size of each of the biocompatible polymer blocks is 10 µm to 300 µm.

5. The method according to claim 1,
wherein a thickness or a diameter of the cell structure is 100 µm to 3 cm.

6. The method according to claim 1,
wherein the biocompatible polymer block is formed of a recombinant peptide.

7. The method according to claim 6,
wherein the recombinant peptide is represented by the following formula, Formula: $A-[(Gly-X-Y)_n]_m-B$ in the formula, A represents any amino acid or any amino acid sequence, B represents any amino acid or any amino acid sequence, n pieces of X each independently represent any amino acid, n pieces of Y each independently represent any amino acid, n represents an integer of 3 to 100, m represents an integer of 2 to 10, and n pieces of Gly-X-Y may be the same as or different from each other.

8. The method according to claim 6,
wherein the recombinant peptide is any one of a peptide which consists of an amino acid sequence described in SEQ ID NO: 1 or a peptide which consists of an amino acid sequence having 80% or more sequence identity with the amino acid sequence described in SEQ ID NO: 1, and has biocompatibility.

9. The method according to claim 1,
wherein in the biocompatible polymer block, the biocompatible polymers are cross-linked by heat, an ultraviolet ray, or an enzyme.

10. The method according to claim 1,
wherein the biocompatible polymer block is in a form of a granule obtained by pulverizing a porous body of the biocompatible polymer.

11. The method according to claim 1,
wherein the lysosomal storage disease is Fabry disease.

12. The method according to claim 1,
wherein an amount of globotriaosylsphingosine in a living body is reduced by secreting α-galactosidase A in the living body.

13. The method according to claim 1, wherein the lysosomal storage disease is not Hurler-Scheie syndrome or Maroteaux-Lamy syndrome.

14. The method according to claim 1, wherein the biocompatible polymer block is a polypeptide.

15. The method according to claim 1, wherein the cells are not hematopoietic stem cells, leukocytes, granulocytes, monocytes, B cells, and T cells.

16. The method according to claim 1, wherein the cells consist of at least a mesenchymal stem cell, and/or a fibroblast.

17. The method according to claim 1, wherein the number of cells transplanted by the cell structure is $1.0 \times 10^5$ cells/kg to $4.0 \times 10^7$ cells/kg.

18. The method according to claim 1, wherein the cell structure is transplanted by an administration via a portal vein or by subcutaneous administration.

19. A method of treating Fabry disease, comprising transplanting a cell structure to a subject in need of a treatment for Fabry disease, wherein the cell structure includes a plurality of biocompatible polymer blocks and a plurality of fibroblast cells, wherein at least one of the polymer blocks is disposed in gaps between the plurality of fibroblast cells,
wherein the cells do not overexpress a gene necessary for a therapy of Fabry disease by introduction of the gene,
wherein the number of mesenchymal stem cells and/or fibroblasts transplanted by the cell structure is $1.0 \times 10^5$ cells/kg to $2.0 \times 10^8$ cells/kg, and
wherein the number of cells to be administered to the subject is $1.0 \times 10^5$ cells/kg to $2.0 \times 10^8$ cells/kg.

* * * * *

SEQUENCE LISTING

<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: Synthetic: Recombinant

<400> SEQUENCE: 1

Gly Ala Pro Gly Ala Pro Gly Leu Gln Gly Ala Pro Gly Leu Gln Gly
1               5                   10                  15

```
Met Pro Gly Glu Arg Gly Ala Ala Gly Leu Pro Gly Pro Lys Gly Glu
             20                  25                  30
Arg Gly Asp Ala Gly Pro Lys Gly Ala Asp Gly Ala Pro Gly Ala Pro
         35                  40                  45
Gly Leu Gln Gly Met Pro Gly Glu Arg Gly Ala Ala Gly Leu Pro Gly
     50                  55                  60
Pro Lys Gly Glu Arg Gly Asp Ala Gly Pro Lys Gly Ala Asp Gly Ala
 65                  70                  75                  80
Pro Gly Lys Asp Gly Val Arg Gly Leu Ala Gly Pro Ile Gly Pro Pro
             85                  90                  95
Gly Glu Arg Gly Ala Ala Gly Leu Pro Gly Pro Lys Gly Glu Arg Gly
         100                 105                 110
Asp Ala Gly Pro Lys Gly Ala Asp Gly Ala Pro Gly Lys Asp Gly Val
         115                 120                 125
Arg Gly Leu Ala Gly Pro Ile Gly Pro Pro Gly Pro Ala Gly Ala Pro
     130                 135                 140
Gly Ala Pro Gly Leu Gln Gly Met Pro Gly Glu Arg Gly Ala Ala Gly
 145                 150                 155                 160
Leu Pro Gly Pro Lys Gly Glu Arg Gly Asp Ala Gly Pro Lys Gly Ala
             165                 170                 175
Asp Gly Ala Pro Gly Lys Asp Gly Val Arg Gly Leu Ala Gly Pro Pro
         180                 185                 190
Gly Ala Pro Gly Leu Gln Gly Ala Pro Gly Leu Gln Gly Met Pro Gly
         195                 200                 205
Glu Arg Gly Ala Ala Gly Leu Pro Gly Pro Lys Gly Glu Arg Gly Asp
         210                 215                 220
Ala Gly Pro Lys Gly Ala Asp Gly Ala Pro Gly Ala Pro Gly Leu Gln
 225                 230                 235                 240
Gly Met Pro Gly Glu Arg Gly Ala Ala Gly Leu Pro Gly Pro Lys Gly
             245                 250                 255
Glu Arg Gly Asp Ala Gly Pro Lys Gly Ala Asp Gly Ala Pro Gly Lys
         260                 265                 270
Asp Gly Val Arg Gly Leu Ala Gly Pro Ile Gly Pro Pro Gly Glu Arg
         275                 280                 285
Gly Ala Ala Gly Leu Pro Gly Pro Lys Gly Glu Arg Gly Asp Ala Gly
     290                 295                 300
Pro Lys Gly Ala Asp Gly Ala Pro Gly Lys Asp Gly Val Arg Gly Leu
 305                 310                 315                 320
Ala Gly Pro Ile Gly Pro Pro Gly Pro Ala Gly Ala Pro Gly Ala Pro
             325                 330                 335
Gly Leu Gln Gly Met Pro Gly Glu Arg Gly Ala Ala Gly Leu Pro Gly
         340                 345                 350
Pro Lys Gly Glu Arg Gly Asp Ala Gly Pro Lys Gly Ala Asp Gly Ala
         355                 360                 365
Pro Gly Lys Asp Gly Val Arg Gly Leu Ala Gly Pro Pro Gly Ala Pro
     370                 375                 380
Gly Leu Gln Gly Ala Pro Gly Leu Gln Gly Met Pro Gly Glu Arg Gly
 385                 390                 395                 400
Ala Ala Gly Leu Pro Gly Pro Lys Gly Glu Arg Gly Asp Ala Gly Pro
             405                 410                 415
Lys Gly Ala Asp Gly Ala Pro Gly Ala Pro Gly Leu Gln Gly Met Pro
         420                 425                 430
```

```
Gly Glu Arg Gly Ala Ala Gly Leu Pro Gly Pro Lys Gly Glu Arg Gly
            435                 440                 445

Asp Ala Gly Pro Lys Gly Ala Asp Gly Ala Pro Gly Lys Asp Gly Val
        450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
            485                 490                 495

Ala Asp Gly Ala Pro Gly Lys Asp Gly Val Arg Gly Leu Ala Gly Pro
        500                 505                 510

Ile Gly Pro Pro Gly Pro Ala Gly Ala Pro Gly Ala Pro Gly Leu Gln
    515                 520                 525

Gly Met Pro Gly Glu Arg Gly Ala Ala Gly Leu Pro Gly Pro Lys Gly
    530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Pro Gly
            565                 570

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 5
```

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 10

Glu Arg Gly Asp
1

<210> SEQ ID NO 11
<211> LENGTH: 571
<212> TYPE: PRT
<213> ORGANISM: Artificial Sequence

```
<220> FEATURE:
<223> OTHER INFORMATION: Synthetic: recombinant gelatin
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
```

```
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
```

```
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (176)..(176)
<223> OTHER INFORMATION: Xaa can be any naturally occurring amino acid
<220> FEATURE:
<221> NAME/KEY: misc_feature
<222> LOCATION: (179)..(179)
```

```
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (230)..(230)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
```

-continued

```
<222> LOCATION: (239)..(239)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (287)..(287)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
```

```
<221> NAME/KEY: misc_feature
<222> LOCATION: (299)..(299)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (314)..(314)
<223> OTHER INFORMATION: Xaa can be any naturally occurring amino acid
<220> FEATURE:
<221> NAME/KEY: misc_feature
<222> LOCATION: (317)..(317)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (332)..(332)
<223> OTHER INFORMATION: Xaa can be any naturally occurring amino acid
<220> FEATURE:
<221> NAME/KEY: misc_feature
<222> LOCATION: (335)..(335)
<223> OTHER INFORMATION: Xaa can be any naturally occurring amino acid
<220> FEATURE:
<221> NAME/KEY: misc_feature
<222> LOCATION: (338)..(338)
<223> OTHER INFORMATION: Xaa can be any naturally occurring amino acid
<220> FEATURE:
<221> NAME/KEY: misc_feature
<222> LOCATION: (341)..(341)
<223> OTHER INFORMATION: Xaa can be any naturally occurring amino acid
<220> FEATURE:
<221> NAME/KEY: misc_feature
<222> LOCATION: (344)..(344)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
<220> FEATURE:
<221> NAME/KEY: misc_feature
<222> LOCATION: (350)..(350)
<223> OTHER INFORMATION: Xaa can be any naturally occurring amino acid
<220> FEATURE:
<221> NAME/KEY: misc_feature
<222> LOCATION: (353)..(353)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid
```

-continued

```
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (374)..(374)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (380)..(380)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (386)..(386)
<223> OTHER INFORMATION: Xaa can be any naturally occurring amino acid
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (395)..(395)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (404)..(404)
<223> OTHER INFORMATION: Xaa can be any naturally occurring amino acid
<220> FEATURE:
<221> NAME/KEY: misc_feature
<222> LOCATION: (407)..(407)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (413)..(413)
<223> OTHER INFORMATION: Xaa can be any naturally occurring amino acid
<220> FEATURE:
<221> NAME/KEY: misc_feature
<222> LOCATION: (416)..(416)
```

```
<223> OTHER INFORMATION: Xaa can be any naturally occurring amino acid
<220> FEATURE:
<221> NAME/KEY: misc_feature
<222> LOCATION: (419)..(419)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (425)..(425)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (434)..(434)
<223> OTHER INFORMATION: Xaa can be any naturally occurring amino acid
<220> FEATURE:
<221> NAME/KEY: misc_feature
<222> LOCATION: (437)..(437)
<223> OTHER INFORMATION: Xaa can be any naturally occurring amino acid
<220> FEATURE:
<221> NAME/KEY: misc_feature
<222> LOCATION: (440)..(440)
<223> OTHER INFORMATION: Xaa can be any naturally occurring amino acid
<220> FEATURE:
<221> NAME/KEY: misc_feature
<222> LOCATION: (443)..(443)
<223> OTHER INFORMATION: Xaa can be any naturally occurring amino acid
<220> FEATURE:
<221> NAME/KEY: misc_feature
<222> LOCATION: (446)..(446)
<223> OTHER INFORMATION: Xaa can be any naturally occurring amino acid
<220> FEATURE:
<221> NAME/KEY: misc_feature
<222> LOCATION: (449)..(449)
<223> OTHER INFORMATION: Xaa can be any naturally occurring amino acid
<220> FEATURE:
<221> NAME/KEY: misc_feature
<222> LOCATION: (452)..(452)
<223> OTHER INFORMATION: Xaa can be any naturally occurring amino acid
<220> FEATURE:
<221> NAME/KEY: misc_feature
<222> LOCATION: (455)..(455)
<223> OTHER INFORMATION: Xaa can be any naturally occurring amino acid
<220> FEATURE:
<221> NAME/KEY: misc_feature
<222> LOCATION: (458)..(458)
<223> OTHER INFORMATION: Xaa can be any naturally occurring amino acid
<220> FEATURE:
<221> NAME/KEY: misc_feature
<222> LOCATION: (461)..(461)
<223> OTHER INFORMATION: Xaa can be any naturally occurring amino acid
<220> FEATURE:
<221> NAME/KEY: misc_feature
<222> LOCATION: (464)..(464)
<223> OTHER INFORMATION: Xaa can be any naturally occurring amino acid
<220> FEATURE:
<221> NAME/KEY: misc_feature
<222> LOCATION: (467)..(467)
<223> OTHER INFORMATION: Xaa can be any naturally occurring amino acid
<220> FEATURE:
<221> NAME/KEY: misc_feature
<222> LOCATION: (470)..(470)
<223> OTHER INFORMATION: Xaa can be any naturally occurring amino acid
<220> FEATURE:
<221> NAME/KEY: misc_feature
<222> LOCATION: (473)..(473)
<223> OTHER INFORMATION: Xaa can be any naturally occurring amino acid
<220> FEATURE:
<221> NAME/KEY: misc_feature
```

```
<222> LOCATION: (476)..(476)
<223> OTHER INFORMATION: Xaa can be any naturally occurring amino acid
<220> FEATURE:
<221> NAME/KEY: misc_feature
<222> LOCATION: (479)..(479)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (485)..(485)
<223> OTHER INFORMATION: Xaa can be any naturally occurring amino acid
<220> FEATURE:
<221> NAME/KEY: misc_feature
<222> LOCATION: (488)..(488)
<223> OTHER INFORMATION: Xaa can be any naturally occurring amino acid
<220> FEATURE:
<221> NAME/KEY: misc_feature
<222> LOCATION: (491)..(491)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (497)..(497)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid
<220> FEATURE:
<221> NAME/KEY: misc_feature
<222> LOCATION: (503)..(503)
<223> OTHER INFORMATION: Xaa can be any naturally occurring amino acid
<220> FEATURE:
<221> NAME/KEY: misc_feature
<222> LOCATION: (506)..(506)
<223> OTHER INFORMATION: Xaa can be any naturally occurring amino acid
<220> FEATURE:
<221> NAME/KEY: misc_feature
<222> LOCATION: (509)..(509)
<223> OTHER INFORMATION: Xaa can be any naturally occurring amino acid
<220> FEATURE:
<221> NAME/KEY: misc_feature
<222> LOCATION: (512)..(512)
<223> OTHER INFORMATION: Xaa can be any naturally occurring amino acid
<220> FEATURE:
<221> NAME/KEY: misc_feature
<222> LOCATION: (515)..(515)
<223> OTHER INFORMATION: Xaa can be any naturally occurring amino acid
<220> FEATURE:
<221> NAME/KEY: misc_feature
<222> LOCATION: (518)..(518)
<223> OTHER INFORMATION: Xaa can be any naturally occurring amino acid
<220> FEATURE:
<221> NAME/KEY: misc_feature
<222> LOCATION: (521)..(521)
<223> OTHER INFORMATION: Xaa can be any naturally occurring amino acid
<220> FEATURE:
<221> NAME/KEY: misc_feature
<222> LOCATION: (524)..(524)
<223> OTHER INFORMATION: Xaa can be any naturally occurring amino acid
<220> FEATURE:
<221> NAME/KEY: misc_feature
<222> LOCATION: (527)..(527)
<223> OTHER INFORMATION: Xaa can be any naturally occurring amino acid
<220> FEATURE:
<221> NAME/KEY: misc_feature
<222> LOCATION: (530)..(530)
<223> OTHER INFORMATION: Xaa can be any naturally occurring amino acid
<220> FEATURE:
<221> NAME/KEY: misc_feature
<222> LOCATION: (533)..(533)
<223> OTHER INFORMATION: Xaa can be any naturally occurring amino acid
<220> FEATURE:
```

-continued

```
<221> NAME/KEY: misc_feature
<222> LOCATION: (536)..(536)
<223> OTHER INFORMATION: Xaa can be any naturally occurring amino acid
<220> FEATURE:
<221> NAME/KEY: misc_feature
<222> LOCATION: (539)..(539)
<223> OTHER INFORMATION: Xaa can be any naturally occurring amino acid
<220> FEATURE:
<221> NAME/KEY: misc_feature
<222> LOCATION: (542)..(542)
<223> OTHER INFORMATION: Xaa can be any naturally occurring amino acid
<220> FEATURE:
<221> NAME/KEY: misc_feature
<222> LOCATION: (545)..(545)
<223> OTHER INFORMATION: Xaa can be any naturally occurring amino acid
<220> FEATURE:
<221> NAME/KEY: misc_feature
<222> LOCATION: (548)..(548)
<223> OTHER INFORMATION: Xaa can be any naturally occurring amino acid
<220> FEATURE:
<221> NAME/KEY: misc_feature
<222> LOCATION: (551)..(551)
<223> OTHER INFORMATION: Xaa can be any naturally occurring amino acid
<220> FEATURE:
<221> NAME/KEY: misc_feature
<222> LOCATION: (554)..(554)
<223> OTHER INFORMATION: Xaa can be any naturally occurring amino acid
<220> FEATURE:
<221> NAME/KEY: misc_feature
<222> LOCATION: (557)..(557)
<223> OTHER INFORMATION: Xaa can be any naturally occurring amino acid
<220> FEATURE:
<221> NAME/KEY: misc_feature
<222> LOCATION: (560)..(560)
<223> OTHER INFORMATION: Xaa can be any naturally occurring amino acid
<220> FEATURE:
<221> NAME/KEY: misc_feature
<222> LOCATION: (563)..(563)
<223> OTHER INFORMATION: Xaa can be any naturally occurring amino acid
<220> FEATURE:
<221> NAME/KEY: misc_feature
<222> LOCATION: (566)..(566)
<223> OTHER INFORMATION: Xaa can be any naturally occurring amino acid
<220> FEATURE:
<221> NAME/KEY: misc_feature
<222> LOCATION: (569)..(569)
<223> OTHER INFORMATION: Xaa can be any naturally occurring amino acid

<400> SEQUENCE: 11

Gly Ala Pro Gly Xaa Tyr Gly Xaa Tyr Gly Xaa Tyr Gly Xaa Tyr Gly
1               5                   10                  15

Xaa Tyr Gly Xaa Tyr Gly Xaa Tyr Gly Xaa Tyr Gly Xaa Tyr Gly Xaa
            20                  25                  30

Tyr Gly Xaa Tyr Gly Xaa Tyr Gly Xaa Tyr Gly Xaa Tyr Gly Xaa Tyr
        35                  40                  45

Gly Xaa Tyr Gly Xaa Tyr Gly Xaa Tyr Gly Xaa Tyr Gly Xaa Tyr Gly
    50                  55                  60

Xaa Tyr Gly Xaa Tyr Gly Xaa Tyr Gly Xaa Tyr Gly Xaa Tyr Gly Xaa
65                  70                  75                  80

Tyr Gly Xaa Tyr Gly Xaa Tyr Gly Xaa Tyr Gly Xaa Tyr Gly Xaa Tyr
                85                  90                  95

Gly Xaa Tyr Gly Xaa Tyr Gly Xaa Tyr Gly Xaa Tyr Gly Xaa Tyr Gly
            100                 105                 110

Xaa Tyr Gly Xaa Tyr Gly Xaa Tyr Gly Xaa Tyr Gly Xaa Tyr Gly Xaa
        115                 120                 125

Tyr Gly Xaa Tyr Gly Xaa Tyr Gly Xaa Tyr Gly Xaa Tyr Gly Xaa Tyr
    130                 135                 140

Gly Xaa Tyr Gly Xaa Tyr Gly Xaa Tyr Gly Xaa Tyr Gly Xaa Tyr Gly
145                 150                 155                 160
```

Xaa Tyr Gly Xaa Tyr Gly Xaa Tyr Gly Xaa Tyr Gly Xaa
            165                 170                 175

Tyr Gly Xaa Tyr Gly Xaa Tyr Gly Xaa Tyr Gly Xaa Tyr
            180                 185                 190

Gly Xaa Tyr Gly Xaa Tyr Gly Xaa Tyr Gly Xaa Tyr Gly
            195                 200                 205

Xaa Tyr Gly Xaa Tyr Gly Xaa Tyr Gly Xaa Tyr Gly Xaa
            210                 215                 220

Tyr Gly Xaa Tyr Gly Xaa Tyr Gly Xaa Tyr Gly Xaa Tyr
225                 230                 235                 240

Gly Xaa Tyr Gly Xaa Tyr Gly Xaa Tyr Gly Xaa Tyr Gly
            245                 250                 255

Xaa Tyr Gly Xaa Tyr Gly Xaa Tyr Gly Xaa Tyr Gly Xaa
            260                 265                 270

Tyr Gly Xaa Tyr Gly Xaa Tyr Gly Xaa Tyr Gly Xaa Tyr
            275                 280                 285

Gly Xaa Tyr Gly Xaa Tyr Gly Xaa Tyr Gly Xaa Tyr Gly
290                 295                 300

Xaa Tyr Gly Xaa Tyr Gly Xaa Tyr Gly Xaa Tyr Gly Xaa
305                 310                 315                 320

Tyr Gly Xaa Tyr Gly Xaa Tyr Gly Xaa Tyr Gly Xaa Tyr
            325                 330                 335

Gly Xaa Tyr Gly Xaa Tyr Gly Xaa Tyr Gly Xaa Tyr Gly
            340                 345                 350

Xaa Tyr Gly Xaa Tyr Gly Xaa Tyr Gly Xaa Tyr Gly Xaa
            355                 360                 365

Tyr Gly Xaa Tyr Gly Xaa Tyr Gly Xaa Tyr Gly Xaa Tyr
            370                 375                 380

Gly Xaa Tyr Gly Xaa Tyr Gly Xaa Tyr Gly Xaa Tyr Gly
385                 390                 395                 400

Xaa Tyr Gly Xaa Tyr Gly Xaa Tyr Gly Xaa Tyr Gly Xaa
            405                 410                 415

Tyr Gly Xaa Tyr Gly Xaa Tyr Gly Xaa Tyr Gly Xaa Tyr
            420                 425                 430

Gly Xaa Tyr Gly Xaa Tyr Gly Xaa Tyr Gly Xaa Tyr Gly
            435                 440                 445

Xaa Tyr Gly Xaa Tyr Gly Xaa Tyr Gly Xaa Tyr Gly Xaa
            450                 455                 460

Tyr Gly Xaa Tyr Gly Xaa Tyr Gly Xaa Tyr Gly Xaa Tyr
465                 470                 475                 480

Gly Xaa Tyr Gly Xaa Tyr Gly Xaa Tyr Gly Xaa Tyr Gly
            485                 490                 495

Xaa Tyr Gly Xaa Tyr Gly Xaa Tyr Gly Xaa Tyr Gly Xaa
            500                 505                 510

Tyr Gly Xaa Tyr Gly Xaa Tyr Gly Xaa Tyr Gly Xaa Tyr
            515                 520                 525

Gly Xaa Tyr Gly Xaa Tyr Gly Xaa Tyr Gly Xaa Tyr Gly
            530                 535                 540

Xaa Tyr Gly Xaa Tyr Gly Xaa Tyr Gly Xaa Tyr Gly Xaa
545                 550                 555                 560

Tyr Gly Xaa Tyr Gly Xaa Tyr Gly Xaa Tyr Gly
            565                 570